US012643913B2

(12) United States Patent　　　　(10) Patent No.:　US 12,643,913 B2
Huckle et al.　　　　　　　　　　　　(45) Date of Patent:　　Jun. 2, 2026

(54) MCL-1 INHIBITOR FORMULATIONS

(71) Applicant: AMGEN INC., Thousand Oaks, CA (US)

(72) Inventors: James E. Huckle, Moorpark, CA (US); Markian M. Stec, Moorpark, CA (US); Tian Wu, Newbury Park, CA (US); Darren L Reid, Belmont, MA (US); Fernando A. Alvarez-Nunez, Newbury Park, CA (US); Sean P. Brown, Half Moon Bay, CA (US)

(73) Assignee: AMGEN INC., Thousand Oaks, CA (US)

( * ) Notice: Subject to any disclaimer, the term of this patent is extended or adjusted under 35 U.S.C. 154(b) by 526 days.

(21) Appl. No.: 18/022,905

(22) PCT Filed: Aug. 24, 2021

(86) PCT No.: PCT/US2021/047237

§ 371 (c)(1),
(2) Date: Feb. 23, 2023

(87) PCT Pub. No.: WO2022/046690

PCT Pub. Date: Mar. 3, 2022

(65) Prior Publication Data

US 2023/0312606 A1　　　Oct. 5, 2023

Related U.S. Application Data

(60) Provisional application No. 63/070,630, filed on Aug. 26, 2020.

(51) Int. Cl.
*C07D 519/00*　　　(2006.01)
*A61K 9/20*　　　　(2006.01)
*A61P 35/00*　　　 (2006.01)

(52) U.S. Cl.
CPC .............. *C07D 519/00* (2013.01); *A61K 9/20* (2013.01); *A61P 35/00* (2018.01); *C07B 2200/13* (2013.01)

(58) Field of Classification Search
None
See application file for complete search history.

(56) References Cited

U.S. PATENT DOCUMENTS

| | | | |
|---|---|---|---|
| 9,562,061 B2 | 2/2017 | Brown | |
| 10,300,075 B2 * | 5/2019 | Brown | .................... A61P 35/00 |
| 2011/0312973 A1 * | 12/2011 | Liepold | ................... A61K 9/10 |
| | | | 514/255.05 |

FOREIGN PATENT DOCUMENTS

WO　　　2018183418　　　10/2018

OTHER PUBLICATIONS

Caenepeel, S. et al. Discovery and preclinical evaluation of AMG 397 [abstract]. In: Proceedings of the Annual Meeting of the American Association for Cancer Research; Apr. 27-28, 2020 and Jun. 22-24. Philadelphia (PA): AACR; Cancer Res 2020; 80 (16 Suppl): Abstract nr 6218 (Aug. 15, 2020). (Year: 2020).*
Baghel et al. Polymeric Amorphous Solid Dispersions: A Review of Amorphization, Crystallization, Stabilization, Solid-State Characterization, and Aqueous Solubilization of BCS Class II Drugs. J. Pharm. Sci. 105, 2527-2544 (2016).*

* cited by examiner

*Primary Examiner* — Jeffrey S Lundgren
*Assistant Examiner* — Sara Elizabeth Townsley

(57)　　　　　　ABSTRACT

Provided herein are solid dispersions comprising AMG 397, methods of preparing the solid dispersion, and pharmaceutical formulations comprising AMG 397.

35 Claims, 15 Drawing Sheets

Figure 15

MCL-1 INHIBITOR FORMULATIONS

CROSS REFERENCES TO RELATED APPLICATIONS

This application is a national stage application under 35 U.S.C. § 371 of International Application No. PCT/US2021/047237, filed internationally on Aug. 24, 2021, and claims priority to and the benefit of U.S. Provisional Application No. 63/070,630, filed on Aug. 26, 2020, which is hereby incorporated by reference in its entirety and for all purposes as if fully set forth herein.

BACKGROUND

Technical Field

The present disclosure relates to pharmaceutical formulations of (1S,3'R,6'R,7'R,8'E,11'S,12'R)-6-chloro-7'-methoxy-11',12'-dinethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0^{3,6}.0^{19,24}]pentacosa[8,16,18,24]tetraen]-15'-one 13',13'-dioxide (AMG 397), a salt, or solvate thereof. AMG 397 is an inhibitor of myeloid cell leukemia 1 protein (Mcl-1). The present disclosure further relates to a solid dispersion comprising amorphous AMG 397 and a polymer, a method of preparing the solid dispersion, a crystalline hydrate form of AMG 397, pharmaceutical formulations thereof, and methods of treating cancer in a subject.

Description of Related Technology

The compound, (1S,3'R,6'R,7'R,8'E,11'S,12'R)-6-chloro-7'-methoxy-11',12'-dinethyl-7'-((9aR)-octahydro-2H-pyrido[1,2-a]pyrazin-2-ylmethyl)-3,4-dihydro-2H,15'H-spiro[naphthalene-1,22'-[20]oxa[13]thia[1,14]diazatetracyclo[14.7.2.0^{3,6}.0^{19,24}]pentacosa[8,16,18,24]tetraen]-15'-one 13',13'-dioxide (AMG 397), is useful as an inhibitor of myeloid cell leukemia 1 (Mcl-1):

(A)

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions. Research has shown that Mcl-1 inhibitors can be useful for the treatment of cancers. Mcl-1 is overexpressed in numerous cancers.

U.S. Pat. No. 10,300,075, which is incorporated herein by reference in its entirety, discloses AMG 397 as an Mcl-1 inhibitor and provides a method for preparing it.

SUMMARY

Provided herein are solid dispersions comprising amorphous AMG 397 or a pharmaceutically acceptable salt or solvate thereof, and a polymer, wherein AMG 397 has a structure Also provided herein are pharmaceutical formulations comprising the solid dispersion as described herein and a pharmaceutically acceptable excipient.

Also provided herein are methods of preparing the solid dispersion as described herein comprising admixing amorphous AMG 397 and the polymer in a solvent to form a solution, and spray-drying the solution to form the solid dispersion.

Also provided herein is a crystalline hydrate form of AMG 397, characterized by solid state $^{13}$C NMR peaks at 13.57, 19.13, 20.39, 24.04, 25.54, 27.75, 30.09, 31.05, 36.84, 38.27, 39.48, 43.15, 49.53, 50.30, 51.84, 54.40, 56.15, 57.28, 57.78, 60.23, 61.80, 65.65, 78.05, 85.23, 115.91, 123.10, 124.60, 128.11, 130.53, 133.18, 133.87, 134.99, 139.72, 141.47, 143.08, 151.76, and 174.30±0.5 ppm.

Also provided herein are pharmaceutical formulations comprising the crystalline hydrate form of AMG 397 as described herein and a pharmaceutically acceptable excipient.

Also provided herein are methods of treating a subject suffering from cancer, comprising administering to the subject a therapeutically effective amount of the pharmaceutical formulation comprising the crystalline hydrate form of AMG 397 as described herein and a pharmaceutically acceptable excipient.

Also provided herein is a crystalline hydrate form of AMG 397, characterized by XRPD pattern peaks at 10.3, 16.3, and 17.1±0.2° 2θ using Cu Kα radiation.

Also provided herein are pharmaceutical formulations comprising the crystalline hydrate form of AMG 397 as described herein and a pharmaceutically acceptable excipient.

Also provided herein are method of treating a subject suffering from cancer, comprising administering to the subject a therapeutically effective amount of the pharmaceutical formulation comprising the crystalline hydrate form of AMG 397 as described herein and a pharmaceutically acceptable excipient.

BRIEF DESCRIPTION OF FIGURES

FIG. 15 depicts a single crystal X-ray crystal structure of crystalline hydrate form of AMG 397.

DETAILED DESCRIPTION

Figure 1:
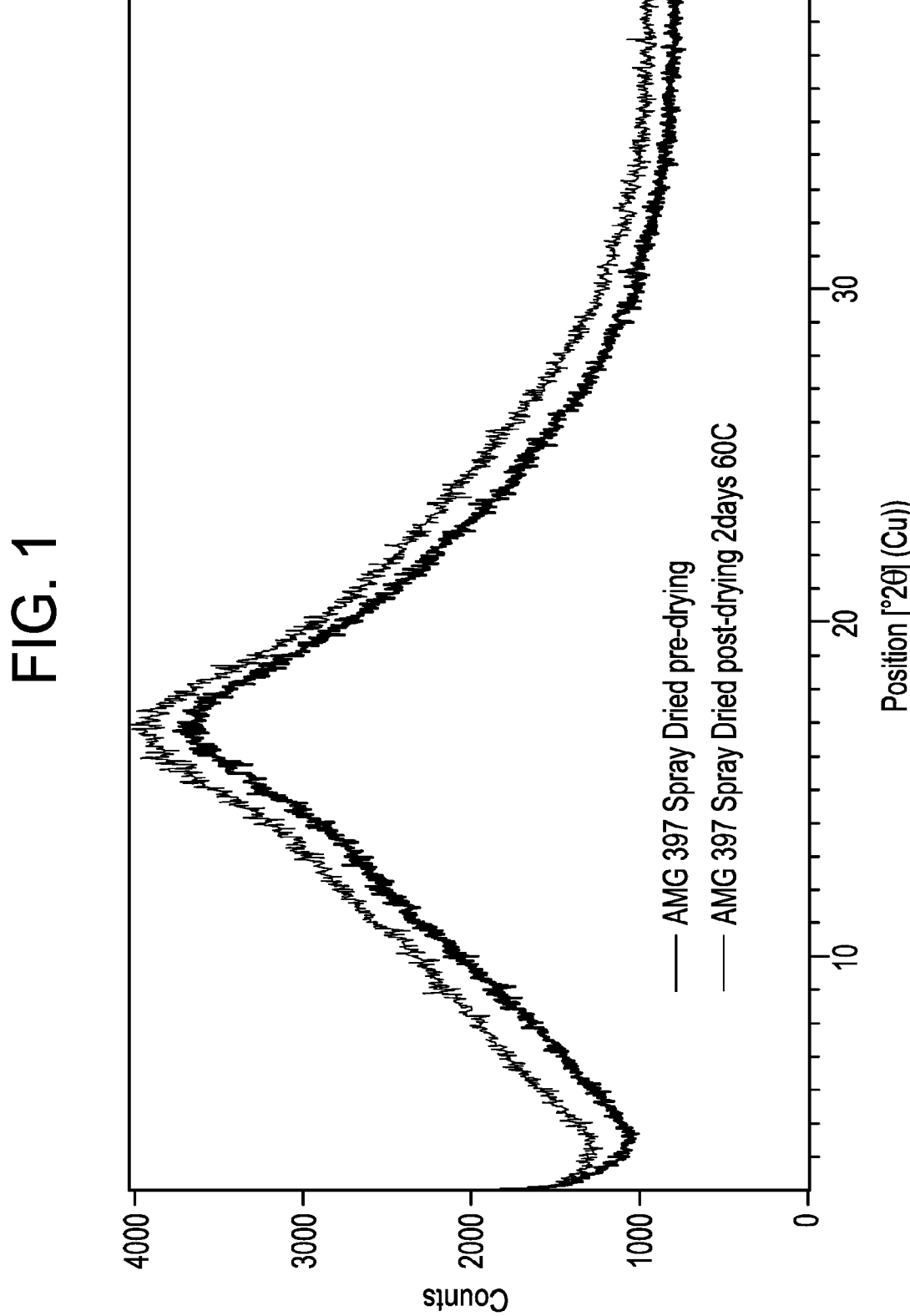
FIG. 1 depicts an X-ray powder diffraction ("XRPD") pattern of the amorphous form of AMG 397.

Provided herein are solid dispersions comprising (1S,3'R, 6'R,7'S,8'E,11'S,12'R)-6-chloro-7'-methoxy-11',12'-dimethyl-3,4-dihydro-2H,15'H-spiro[naphthalene-1,22'[20]oxa[13]thia[1,14]diazatetracyclo[14.7.2.0³,⁶.0¹⁹,²⁴]pentacosa[8,16,18,24]tetraen]-15'-one 13',13'-dioxide (AMG 397), or a pharmaceutically acceptable salt or solvate thereof, and a polymer, wherein AMG 397 has a structure

4

U.S. Pat. No. 10,300,075, which is incorporated herein by reference in its entirety, describes AMG 397, its activity as an Mcl-1 inhibitor, and disclosed how to make AMG 397.

Also disclosed herein are pharmaceutical formulations thereof that include the solid dispersion and methods of treating a subject suffering from cancer, comprising administering to the subject a therapeutically effective amount of the pharmaceutical formulation. The solid dispersion provides benefits, including, but not limited to, higher oral bioavailability compared with other forms of AMG 397, better stability when stored under various conditions, and less variability of bioavailability when there are changes in stomach pH, whereas other formulations, such as the crystalline hydrate form of AMG 397, show up to a 2-fold decrease in bioavailability when stomach pH was outside of the normal range.

Provided herein are methods of preparing the solid dispersion disclosed herein, wherein the methods can comprise admixing amorphous AMG 397 and the polymer in a solvent to form a solution, and spray-drying the solution to form the solid dispersion.

Further provided herein is a crystalline hydrate form of AMG 397, pharmaceutical formulations thereof, and methods of treating a subject suffering from cancer, comprising administering to the subject a therapeutically effective amount of the pharmaceutical formulation.

The formulations, dosage presentations, and methods are contemplated to include embodiments including any combination of one or more of the additional optional elements, features, and steps further described below (including those shown in the Tables), unless stated otherwise.

Unless otherwise specified, the following definitions apply to terms found in the specification and claims:

"Treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of treatment, such as, for example, cancer.

The term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

"Pharmaceutically acceptable salts" include, but are not limited to salts with inorganic acids, such as hydrochlorate (i.e., hydrochloride), phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate. HOOC—$(CH_2)_n$—COOH where n is 0-4, and like salts. Similarly, pharmaceutically acceptable cations include, but are not limited to sodium, potassium, calcium, aluminum, lithium, and ammonium. Those skilled in the art will recognize various synthetic methodologies that may be used to prepare non-toxic pharmaceutically acceptable addition salts.

The term "hydrate" refers to the chemical entity formed by the interaction of water and a compound, including, for example, hemi-hydrates, monohydrates, dihydrates, trihydrates, etc. Solvates of AMG 397 used in formulations herein are within the scope of the invention. A hydrate, as used herein, can have a variable amount of water, such as, 0.6 to 2 water molecules per AMG 397 molecule.

"Crystalline form" and "polymorph may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Solid Dispersions

Provided herein are solid dispersions comprising amorphous AMG 397 or a pharmaceutically acceptable salt or solvate thereof, and a polymer, wherein AMG 397 has a structure The solid dispersion disclosed herein comprises AMG 397 in an amorphous form. The amorphous AMG 397 can be characterized by an X-ray powder diffraction (XRPD) pattern substantially as shown in FIG. 1, wherein "substantially" is meant that the reported peaks can vary by ±0.2°.

Figure 2:
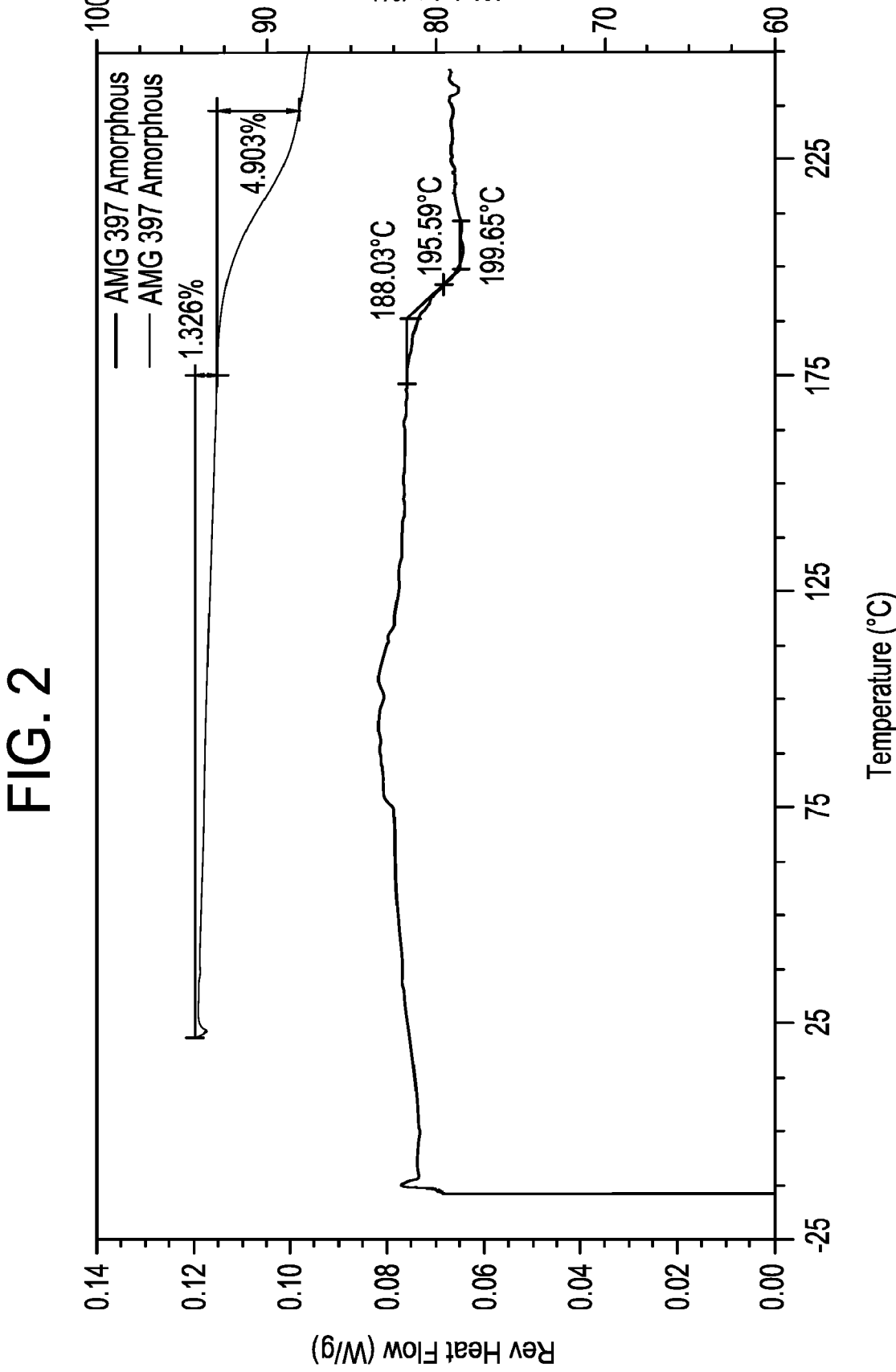
FIG. 2 depicts a differential scanning calorimetry ("DSC") thermograph of the amorphous form of AMG 397 and a thermogravimetric analysis ("TGA") trace of the amorphous form of AMG 397.

The amorphous AMG 397 also can be characterized by thermogravimetric analysis (TGA). Thus, the amorphous AMG 397 can be characterized by a weight loss in a range of about 0% to about 5% with an onset temperature of 188° C. to 205° C. In some embodiments, the amorphous AMG 397 can be characterized by a weight loss in a range of about 0% to about 5% with an onset temperature at 196° C.±3° C. For example, the amorphous AMG 397 can be characterized by a weight loss of 1.3% associated with the dehydration (water content was 1.6% by Karl Fischer titration) and weight loss of 4.9% after passing through the glass transition ("Tg"). In some embodiments, the crystalline hydrate form of AMG 397 has a TGA substantially as depicted in FIG. 2, wherein by "substantially" is meant that the reported TGA features can vary by ±5° C.

Differential scanning calorimetry (DSC) thermographs were obtained of amorphous AMG 397. The DSC curve indicates an endothermic transition at 196° C.±3° C. Thus, in some embodiments, amorphous AMG 397 can be characterized by a DSC thermograph having an endothermic transition at 188° C. to 205° C. In some embodiments, amorphous AMG 397 is characterized by DSC, as shown in FIG. 2.

Figure 3:
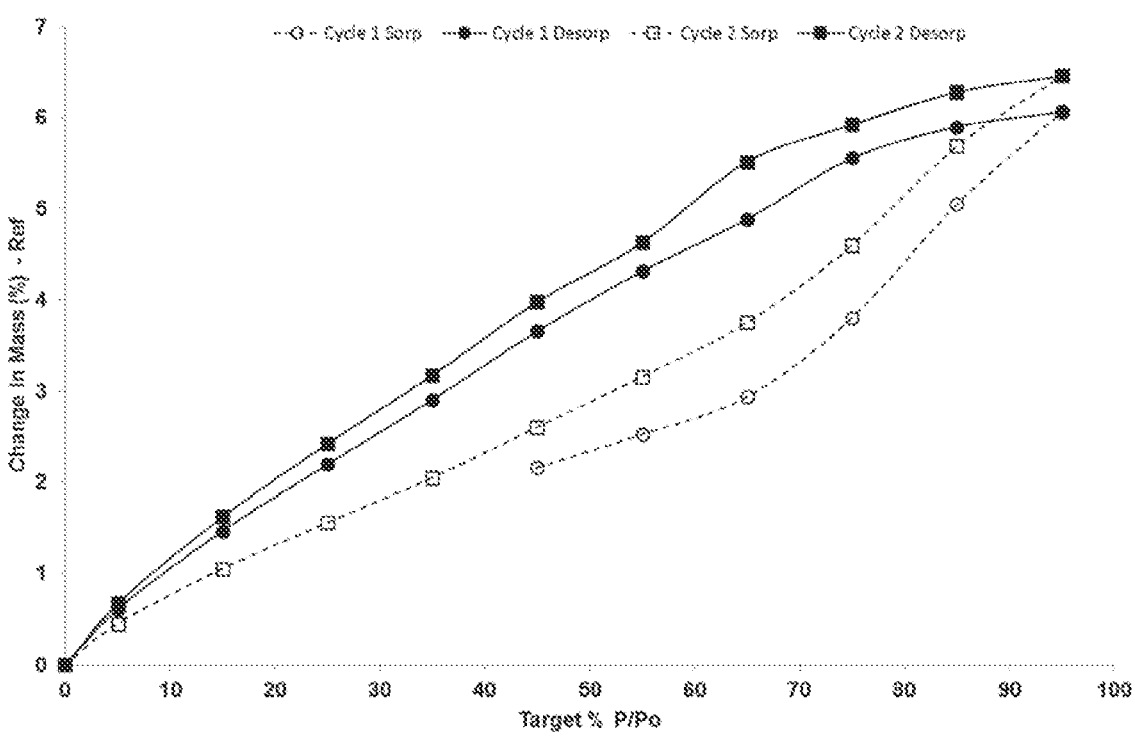
FIG. 3 depicts a moisture sorption profile of the amorphous form of AMG 397.

The amorphous AMG 397 can also be characterized by a moisture sorption profile. For example, in some embodiments amorphous AMG 397 is characterized by the moisture sorption profile as shown in FIG. 3, showing a weight gain of ~6.4% by 95% RH.

Figure 4:
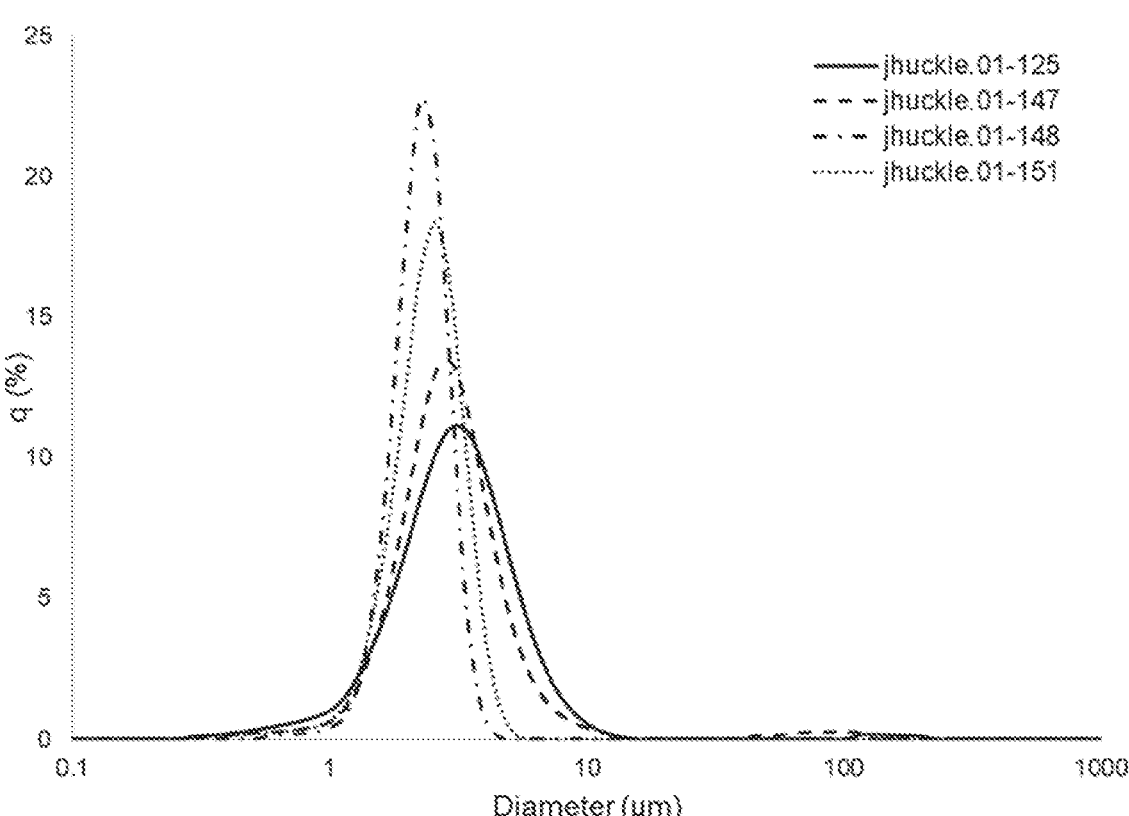
FIG. 4 depicts a graph of the particle size distribution of the amorphous form of AMG 397.

The amorphous AMG 397 can still further be characterized by particle size distribution. In some embodiments, the amorphous AMG 397 can have a D10 particle size of 2 μm or less. In some embodiments, the amorphous AMG 397 can have a D10 particle size of 1.6 μm or less. In some embodiments, the amorphous AMG 397 can have a D50 particle size of 3 μm or less, such as, 3 μm, 2.5 μm, 2 μm, 1.5 μm, 1 μm, or 0.5 μm. In some embodiments, the amorphous AMG 397 can have a D90 particle size of 7 μm or less, such as 7 μm, 6.5 μm, 6 μm, 5.5 μm, 5 μm, 4 μm, 3 μm, 2 μm, or 1 μm. For example, in some embodiments, the amorphous AMG 397 can have a particle size distribution as shown in FIG. 4. Particle size distribution can be measured by, e.g., laser diffraction.

The polymer in the solid dispersion can be any polymer known to one of skill in the art, which can stabilize the amorphous AMG 397 and/or provide better bioavailability to amorphous AMG 397. In some embodiments, the polymer can comprise pulluan, dextrin, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate dimethylaminoacetate, a copolymer of vinyl diethylamine/vinyl acetate, a copolymer of vinyl benzylamine/vinyl acetate, polyvinyl acetaldiethylamino acetate, a copolymer of vinylpiperidylacetoacetaVvinyl acetate, polydiethylaminomethylstyrene, a copolymer of methyl methacrylate/butyl methacrylate/dimethylaminoethyl methacrylate and polydimethylaminoethylmethacrylate, a copolymer of 2-methyl-5- vinylpyridine/methylmethacrylate/methacrylic acid, a copolymer of 2-methyl-5-vinylpyridine/methyl acrylate/ methacrylic acid, a copolymer of 2-vinyl-5-ethylpyridine/ methacrylic acid/methy acrylate, a copolymer of 2-vinylpyrid-ine/methacrylic acid/acrylonitrile, carboxymethylpiperidyl starch, carboxy-methylbenzylaminocellulose, a copolymer of N-vinylglycine/styrene, chitosan, poly(vinyl alcohol), maleic anhydride copolymer, poly(vinyl pyrolidone), starch, starch-based polymer, poly(2-ethyl-2-oxazoline), poly(ethyleneimine), polyurethane hydrogel, welan gum, rhamsan gum, polyvinyl acetate, ethylcellulose, eudragit RL, eudragit RS, eudragit NE 30D, Kollicoat EMM 30D, or a combination thereof. In some embodiments, the polymer can comprise hydroxypropyl methylcellulose, hydroxypropylmethylcellulose acetate succinate, polyvinylpyrrolidone, polyvinyl alcohol, poly(vinyl pyrrolidone), hydroxypropylcellulose. In some embodiments, the polymer comprises hydroxypropyl methylcellulose (HPMC).

The solid dispersion disclosed herein can comprise any amount of amorphous AMG 397 or a pharmaceutically acceptable salt or solvate thereof, based on the total weight of the solid dispersion. Specifically contemplated amounts of amorphous AMG 397 include the amorphous AMG 397 being present in an amount of 1% to 90% by weight, based on the total weight of the solid dispersion, such as 5% to 80%, or 10% to 70%, or 20% to 60%, or 30% to 60%, or 40% to 60% or 50% to 60% by weight, based on the total weight of the solid dispersion. In some embodiments, the solid dispersion can include the amorphous AMG 397 and the polymer present in 50 wt % each, based on the total weight of the solid dispersion. In some embodiments, the solid dispersion can include the amorphous AMG 397 present in 25 wt % and the polymer present in 75 wt %. In some embodiments, the solid dispersion can include the amorphous AMG 397 present in 75 wt % and the polymer present in 25 wt %. For example, the solid dispersion can include the amorphous AMG 397 present in 10 wt %, 20 wt %, 25 wt %, 30 wt %, 40 wt %, 50 wt %, 60 wt %, 70 wt %, 75 wt %, 80 wt %, 90 wt %, or 95 wt %. For example, the solid dispersion can include the polymer present in 10 wt %, 20 wt %, 25 wt %, 30 wt %, 40 wt %, 50 wt %, 60 wt %, 70 wt %, 75 wt %, 80 wt %, 90 wt %, or 95 wt %.

The solid dispersion disclosed herein has improved stability over other forms of AMG 397. In some embodiments, the solid dispersion exhibits stability (as measured by amount of impurities formed during storage). In various embodiments, the solid dispersion exhibits a stability such that the amount of impurities formed are less than 10% upon storage at 40° C. and 75% relative humidity in an open container for 1 month. For example, the solid dispersion can have a stability such that less than 9% impurities form, less than 8% impurities form, less than 7% impurities form, less than 6% impurities form, less than 5% impurities form, less than 4% impurities form, less than 3% impurities form, or less than 2% impurities form when stored at 40° C. and 75% relative humidity in an open container for 1 month. For example, the solid dispersion can have a stability such that less than 3% impurities form when stored at 40° C. and 75% relative humidity in a closed container for 1 month. For example, the solid dispersion can have a stability such that less than 2% impurities form when stored at 40° C. and 75% relative humidity in a closed container for 1 month.

Pharmaceutical Formulation

Provided herein are pharmaceutical formulations comprising the solid dispersions as described herein and a pharmaceutically acceptable excipient. In some embodiments, the pharmaceutical formulation is in the form of a tablet. In some embodiments, the pharmaceutical formulation is in the form of an immediate release tablet. Solid oral drug compositions (e.g., tablets) or preparations have various release profiles, such as an immediate release profile as referenced by FDA guidelines ("Dissolution Testing of Immediate Release Solid Oral Dosage Forms", issued August 1997, Section IV-A). In the dissolution testing guideline for immediate release profiles, materials which dissolve at least 80% in the first 30 to 60 minutes in solution qualify as immediate release profiles. Therefore, immediate release solid dosage forms permit the release of most or all of the active ingredient over a short period of time, such as 60 minutes or less, and make rapid absorption of the drug possible. In contrast, extended release solid oral dosage forms permit the release of the active ingredient over an extended period of time in an effort to maintain therapeutically effective plasma levels over similarly extended time intervals, improve dosing compliance, and/or to modify other pharmacokinetic properties of the active ingredient.

"Pharmaceutically acceptable excipient" refers to a broad range of ingredients that may be combined with a compound or salt of the present invention to prepare a pharmaceutical composition or formulation. Excipients are additives that are included in a formulation because they either impart or enhance the stability, delivery and manufacturability of a drug product, and are physiologically innocuous to the recipient thereof. Regardless of the reason for their inclusion, excipients are an integral component of a drug product and therefore need to be safe and well tolerated by patients. Given the teachings and guidance provided herein, those skilled in the art will readily be able to vary the amount or range of excipient without increasing viscosity to an undesirable level. Excipients may be chosen to achieve a desired bioavailability, desired stability, resistance to aggregation or degradation or precipitation, protection under conditions of freezing, lyophilization or high temperatures, or other properties. Typically, excipients include, but are not limited to, diluents, colorants, vehicles, anti-adherants, glidants, disintegrants, flavoring agents, coatings, binders, sweeteners, lubricants, sorbents, preservatives, and the like. Examples of suitable excipients are well known to the person skilled in the art of tablet formulation and may be found e.g. in *Handbook of Pharmaceutical Excipients* (eds. Rowe, Sheskey & Quinn), 6th edition 2009.

As used herein the term "excipients" is intended to refer to inter alia basifying agents, solubilizers, glidants, fillers, binders, lubricant, diluents, preservatives, surface active agents, dispersing agents and the like. The term also includes agents such as sweetening agents, flavoring agents, coloring agents and preserving agents. Such components will generally be present in admixture within the tablet.

Examples of solubilizers include, but are not limited to, ionic surfactants (including both ionic and non-ionic surfactants) such as sodium lauryl sulphate, cetyltrimethylammonium bromide, polysorbates (such as polysorbate 20 or 80), poloxamers (such as poloxamer 188 or 207), and macrogols.

Examples of lubricants, glidants and flow aids include, but are not limited to, magnesium stearate, calcium stearate, stearic acid, hydrogenated vegetable oil, glyceryl palmitostearate, glyceryl behenate, sodium stearyl fumarate, colloidal silicon dioxide, and talc. The amount of lubricant in a tablet can generally be between 0.1-5% by weight.

Examples of disintegrants include, but are not limited to, starches, celluloses, cross-linked PVP, sodium starch glycolate, croscarmellose sodium, etc.

Examples of fillers (also known as bulking agents or diluents) include, but are not limited to, starches, maltodextrins, polyols (such as lactose), and celluloses. Tablets provided herein may include lactose and/or microcrystalline cellulose. Lactose can be used in anhydrous or hydrated form (e.g. monohydrate), and is typically prepared by spray drying, fluid bed granulation, or roller drying.

Examples of binders include, but are not limited to, cross-linked PVP, HPMC, microcrystalline cellulose, sucrose, starches, etc.

In embodiments, the pharmaceutically acceptable excipients can comprise one or more diluent, binder, or disintegrant. In embodiments, the pharmaceutically acceptable excipients can comprise a diluent comprising one or more of microcrystalline cellulose, starch, dicalcium phosphate, lactose, sorbitol, mannitol, sucrose, and methyl dextrins, a binder comprising one or more of povidone, hydroxypropyl methylcellulose, hydroxypropyl cellulose, and sodium carboxymethylcellulose, and a disintegrant comprising one or more of crospovidine, sodium starch glycolate, and croscarmellose sodium.

Tablets provided herein may be uncoated or coated (in which case they include a coating). Although uncoated tablets may be used, it is more usual to provide a coated tablet, in which case a conventional non-enteric coating may be used. Film coatings are known in the art and can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though the water soluble material included in the film coating of the present invention may include a single polymer material, it may also be formed using a mixture of more than one polymer. The coating may be white or colored e.g. gray. Suitable coatings include, but are not limited to, polymeric film coatings such as those comprising polyvinyl alcohol e.g. 'Opadry® II' (which includes part-hydrolysed PVA, titanium dioxide, macrogol 3350 and talc, with optional coloring such as iron oxide or indigo carmine or iron oxide yellow or FD&C yellow #6). The amount of coating will generally be between 2-4% of the core's weight, and in certain specific embodiments, 3%. Unless specifically stated otherwise, where the dosage form is coated, it is to be understood that a reference to % weight of the tablet means that of the total tablet, i.e. including the coating.

The pharmaceutical formulations disclosed herein can further comprise a surfactant. As used herein, the surfactant can be cationic, anionic, or non-ionic. In some embodiments, the pharmaceutical formulation can comprise a non-ionic surfactant. In some embodiments, the surfactant can comprise a polysorbate, a poloxamer, or a combination thereof. In some embodiments, the surfactant can comprise polysorbate 20, polysorbate 60, polysorbate 80, or a combination thereof.

The pharmaceutical formulations disclosed herein exhibit improved bioavailability of AMG 397, compared to other formulations of AMG 397. In some embodiments, the AMG 397 of the disclosed pharmaceutical formulations exhibits a bioavailability (% F) of at least 15% within 24 hours, as assessed in a beagle dog PK study over 48 hours, as described in the Examples below. In some embodiments, the AMG 397 of the disclosed pharmaceutical formulations exhibits a bioavailability (% F) of at least 15% within 24 hours, as assessed in a beagle dog PK study over 48 hours, as described in the Examples below. For example, the bioavailability of AMG 397 in the disclosed pharmaceutical formulations can be 15%, 17.5%, 20%, 22.5%, 25%, 30% or more, as assessed in a beagle dog PK study over 48 hours, as described in the Examples below.

Cancer patients often have a much more basic stomach environment than a healthy patient (e.g., greater than 5 pH, or a pH of 6 to 7). However, not all cancer patients exhibit such a basic stomach environment. As such, development of a pharmaceutical formulation that exhibits comparable bioavailability of a chemotherapeutic at either typical stomach pHs (e.g., pH of 2 to 3) as well as a more basic stomach pH (e.g., pH of 6 to 7) provides the clinician better certainty of knowledge of how the patient will be exposed to the chemotherapeutic. In some embodiments, the pharmaceutical formulations disclosed herein can provide a bioavailability (% F) of AMG 397 of at least 15% when a subject's stomach is at a pH of 6-7. In some embodiments, the pharmaceutical formulations disclosed herein can provide a bioavailability (% F) of amorphous AMG 397 of at least 15% when a subject's stomach is at a pH of 2-3.

Similar to the variability of cancer patients' stomach pHs, some cancer patients are administered P-gp inhibitors which can impact a chemotherapeutic's release profile in the stomach. In some embodiments, the pharmaceutical formulations disclosed herein can provide a bioavailability of amorphous AMG 397 of at least 25% within 48 hours, as assessed in a beagle dog PK study over 48 hours, when co-administered with P-gp inhibitor.

Methods of Preparing the Solid Dispersion

Further provided herein are methods of preparing the solid dispersion as disclosed herein. The methods comprise admixing amorphous AMG 397 and the polymer disclosed herein in a solvent to form a solution, and spray drying the solution to form the solid dispersion.

In general, the solvent can include an organic solvent and/or water. In some embodiments, the solvent can comprise water, methanol, ethanol, dichloromethane (DCM), acetone, tetrahydrofuran (THF), ethyl acetate, chloroform, dimethyl formamide, dimethyl sulfoxide, glycerin, or a combination thereof. In some embodiments, the solvent can comprise an aprotic organic solvent. In some embodiments, the solvent can include a co-solvent. In some embodiments, the solvent can comprise water and methanol, ethanol, dichloromethane (DCM), acetone, tetrahydrofuran (THF), ethyl acetate, chloroform, dimethyl formamide, dimethyl sulfoxide, glycerin, or a combination thereof. In some embodiments, the solvent can comprise water and DCM, THF, or a combination of DCM and THF. In some embodiments, the solvent comprises DCM, THF, or a combination thereof. In some embodiments, the solvent is DCM or DCM and water. In some embodiments, the solvent is THF or THF and water.

In some embodiments, the solution can be spray dried at any suitable mL/min rate suitable to one of ordinary skill in the art. In some embodiments, the solution can be spray dried at a rate of 0.1 mL/min to 10 mL/min, such as 0.1 mL/min, 0.5 mL/min, 1 mL/min, 1.5 mL/min, 2 mL/min, 2.5 mL/min, 3 mL/min, 3.5 mL/min, 4 mL/min, 5 mL/min, 6 mL/min, 7 mL/min, 8 mL/min, 9 mL/min, or 10 mL/min.

The methods of preparing the solid dispersion disclosed herein can further include drying the solid dispersion, after spray drying. In some embodiments, the solid dispersion can be dried under vacuum at a pressure of 1 mmHg to 700 mmHg, such as, 10 mmHg. In some embodiments, the solid dispersion can be dried at elevated temperatures, such as 30° C. to 100° C., or 40° C. to 90° C., or 50° C. to 70° C. For example, the solid dispersion can be dried at a temperature of 60° C. In some embodiments, the solid dispersion can be dried for an extended period of time, such as 12 hours to 72 hours, or 16 hours to 60 hours, or 24 hours to 48 hours. For example, the solid dispersion can be dried for 48 hours.

In some embodiments, the solid dispersion provided from the methods of preparing a solid dispersion can be formulated into a pharmaceutical formulation, such as the pharmaceutical formulations described herein.

Crystalline Hydrate Form

Figure 14:
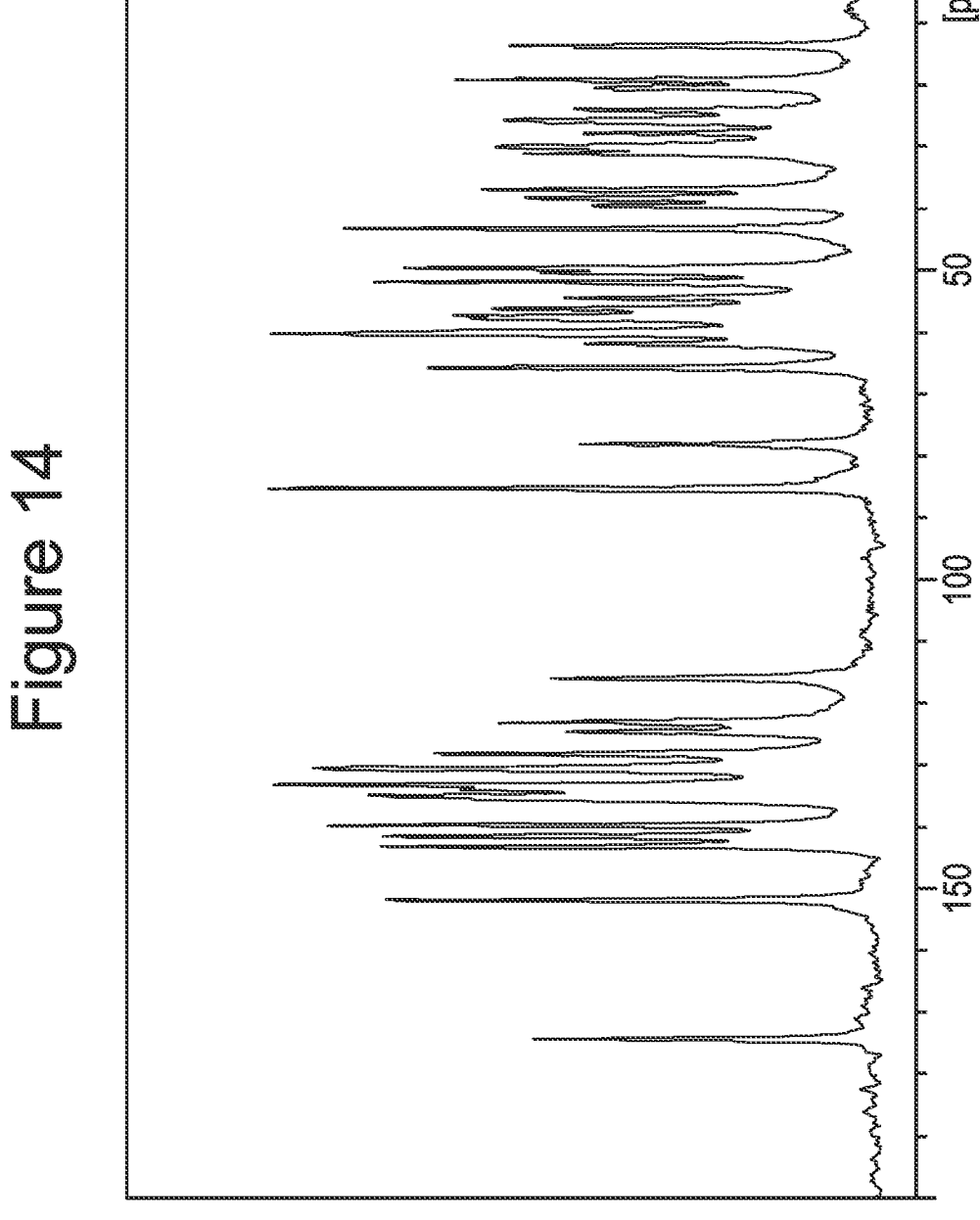
FIG. 14 depicts a solid state $^{13}$C NMR of the crystalline hydrate form of AMG 397.

Also provided herein is a crystalline hydrate form of AMG 397. The crystalline hydrate form of AMG 397 can be characterized by solid state $^{13}$C NMR, obtained as set forth in the Examples, having peaks at 13.57, 19.13, 20.39, 24.04, 25.54, 27.75, 30.09, 31.05, 36.84, 38.27, 39.48, 43.15, 49.53, 50.30, 51.84, 54.40, 56.15, 57.28, 57.78, 60.23, 61.80, 65.65, 78.05, 85.23, 115.91, 123.10, 124.60, 128.11, 130.53, 133.18, 133.87, 134.99, 139.72, 141.47, 143.08, 151.76, and 174.30±0.5 ppm. In some embodiments, the crystalline hydrate form of AMG 397 has a solid state $^{13}$C NMR substantially as shown in FIG. 14, wherein by "substantially" is meant that the reported peaks can vary by ±0.5 ppm.

Figure 10:
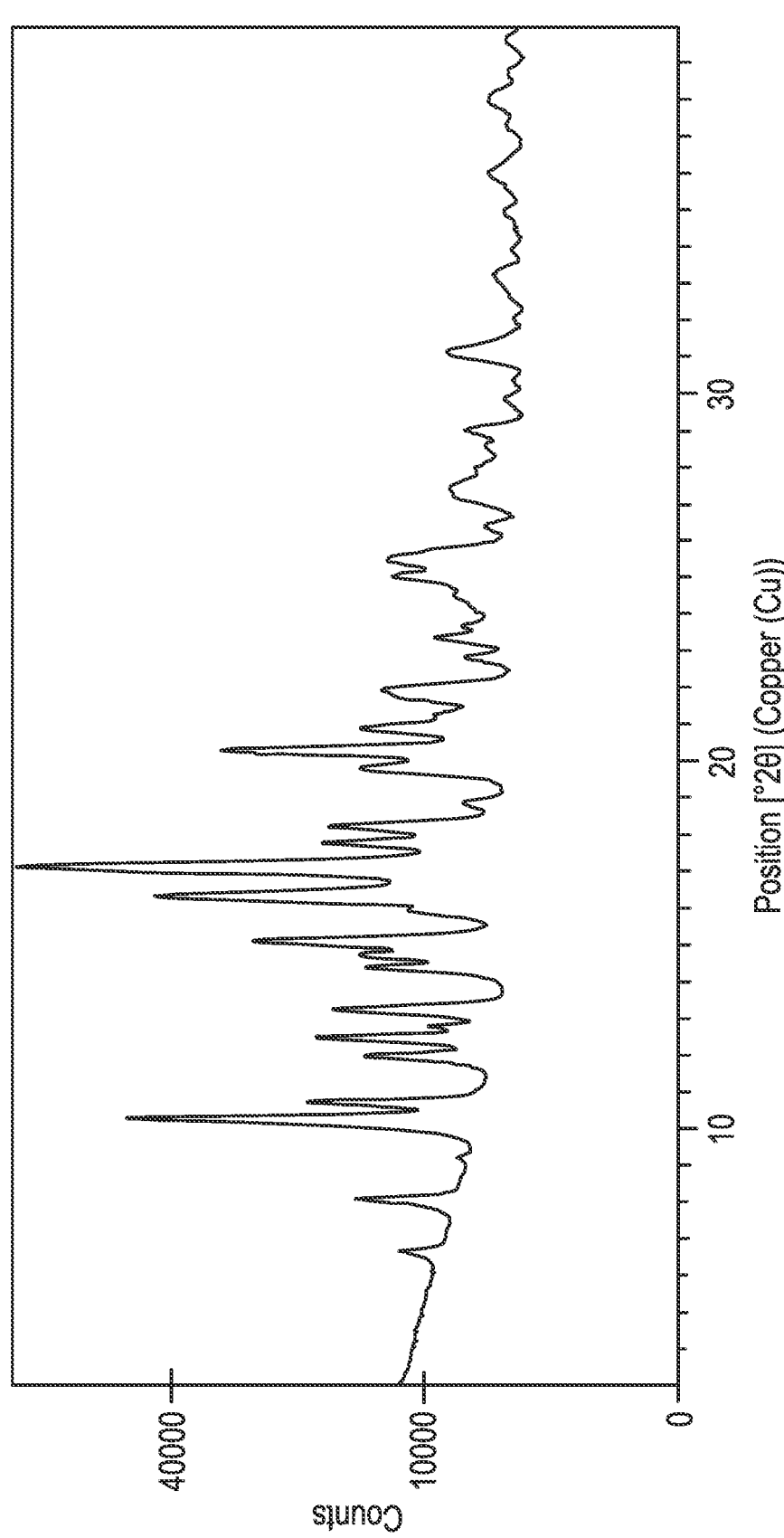
FIG. 10 depicts an X-ray powder diffraction ("XRPD") pattern of the crystalline hydrate form of AMG 397.

The crystalline hydrate form of AMG 397 can be further characterized by an X-ray powder diffraction pattern, obtained as set forth in the Examples, having peaks at 10.3, 16.3, and 17.1±0.2° 2θ using Cu Kα radiation. The crystalline hydrate form of AMG 397 optionally can be further characterized by an X-ray powder diffraction pattern having additional peaks at 8.23, 24.40, 25.03, 25.49, and 32.03±0.2° 2θ using Cu Kα radiation. The crystalline hydrate form of AMG 397 optionally can be further characterized by an X-ray powder diffraction pattern having additional peaks at 14.4, 14.7, 15.9, 17.7, 18.1, 19.8, 20.9, 21.7, 21.9, and 25.0±0.2° 2θ using Cu Kα radiation. In some embodiments, crystalline hydrate form of AMG 397 has an X-ray powder diffraction pattern substantially as shown in FIG. 10, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 11:
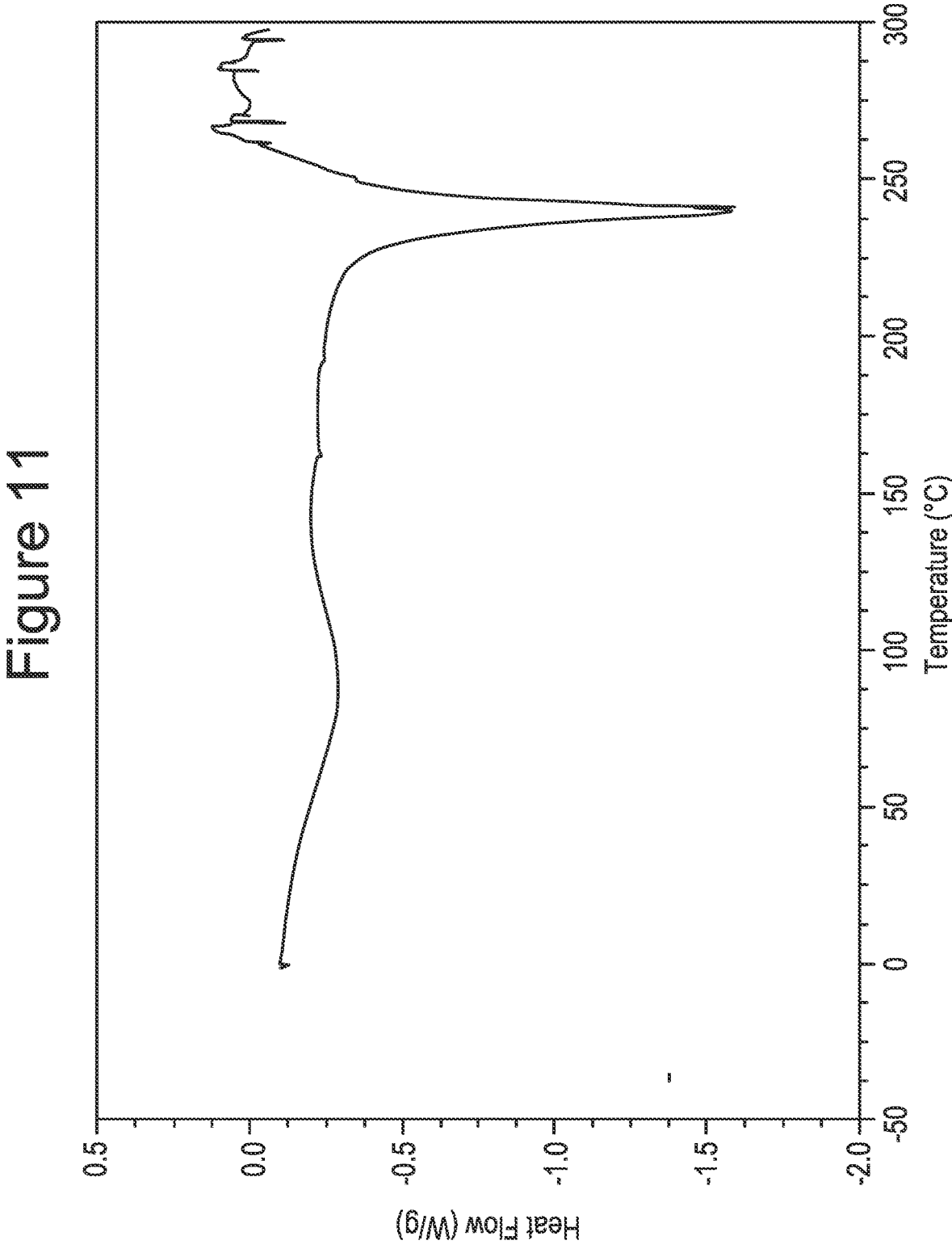
FIG. 11 depicts a TGA trace of the crystalline hydrate form of AMG 397.

Differential scanning calorimetry (DSC) thermographs were obtained, as set forth in the Examples, for the crystalline hydrate form of AMG 397. The DSC curve indicates an endothermic transition at 221° C.±3° C. Thus, in some embodiments, the crystalline hydrate form of AMG 397 can be characterized by a DSC thermograph having a transition endotherm with an onset of 218° C. to 224° C. For example, in some embodiments the crystalline hydrate form of AMG 397 is characterized by DSC, as shown in FIG. 11.

Figure 12:
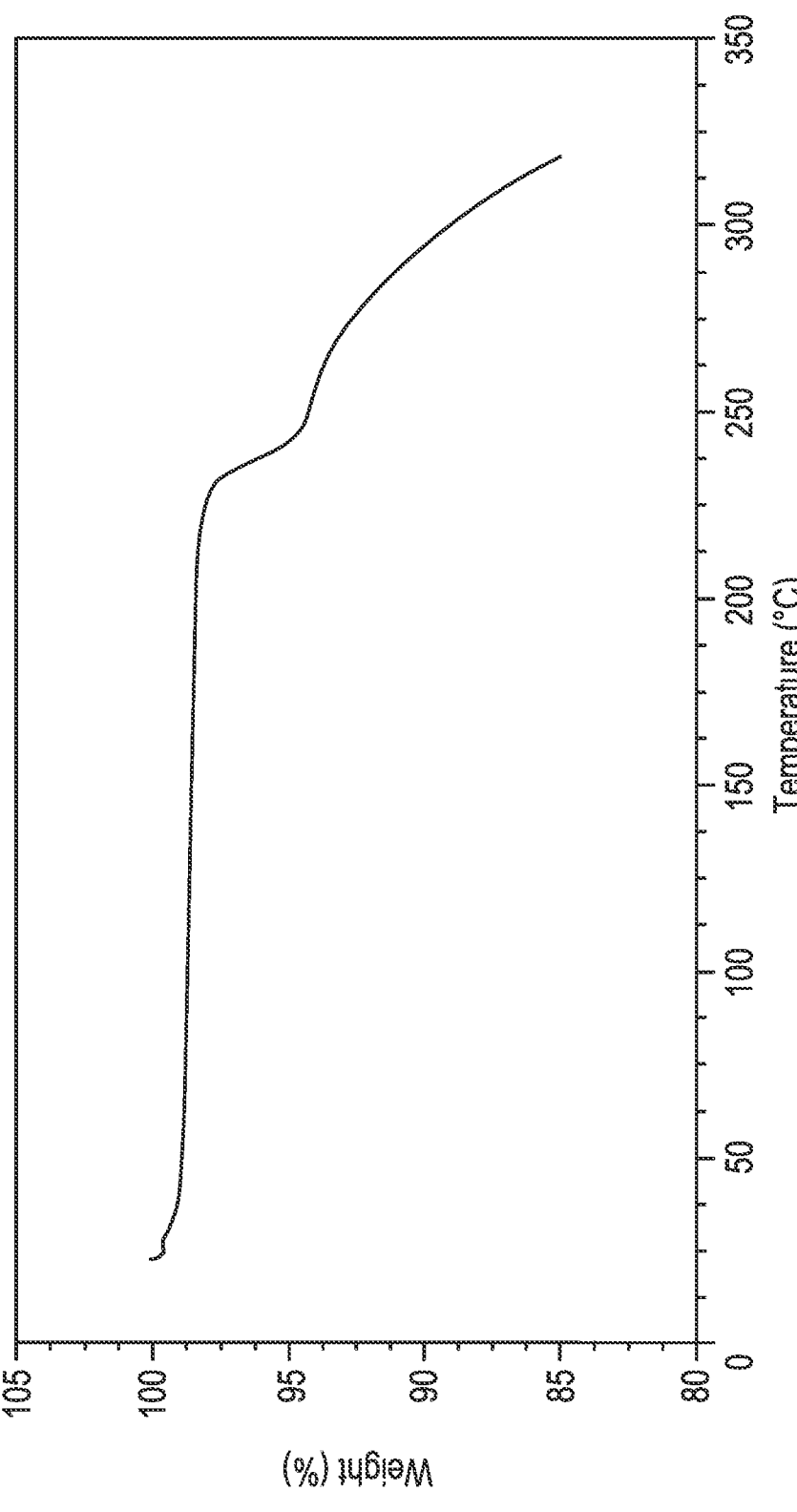
FIG. 12 depicts a DSC thermograph of the crystalline hydrate form of AMG 397.

The crystalline hydrate form of AMG 397 also can be characterized by thermogravimetric analysis (TGA). Thus, the crystalline hydrate form of AMG 397 can be characterized by a weight loss in a range of about 0% to about 3% with an onset temperature of 218° C. to 224° C. For example, the crystalline hydrate form of AMG 397 can be characterized by a weight loss of about 2%, up to about 200° C. In some embodiments, the crystalline hydrate form of AMG 397 has a thermogravimetric analysis substantially as depicted in FIG. 12, wherein by "substantially" is meant that the reported TGA features can vary by ±5° C.

Figure 13:
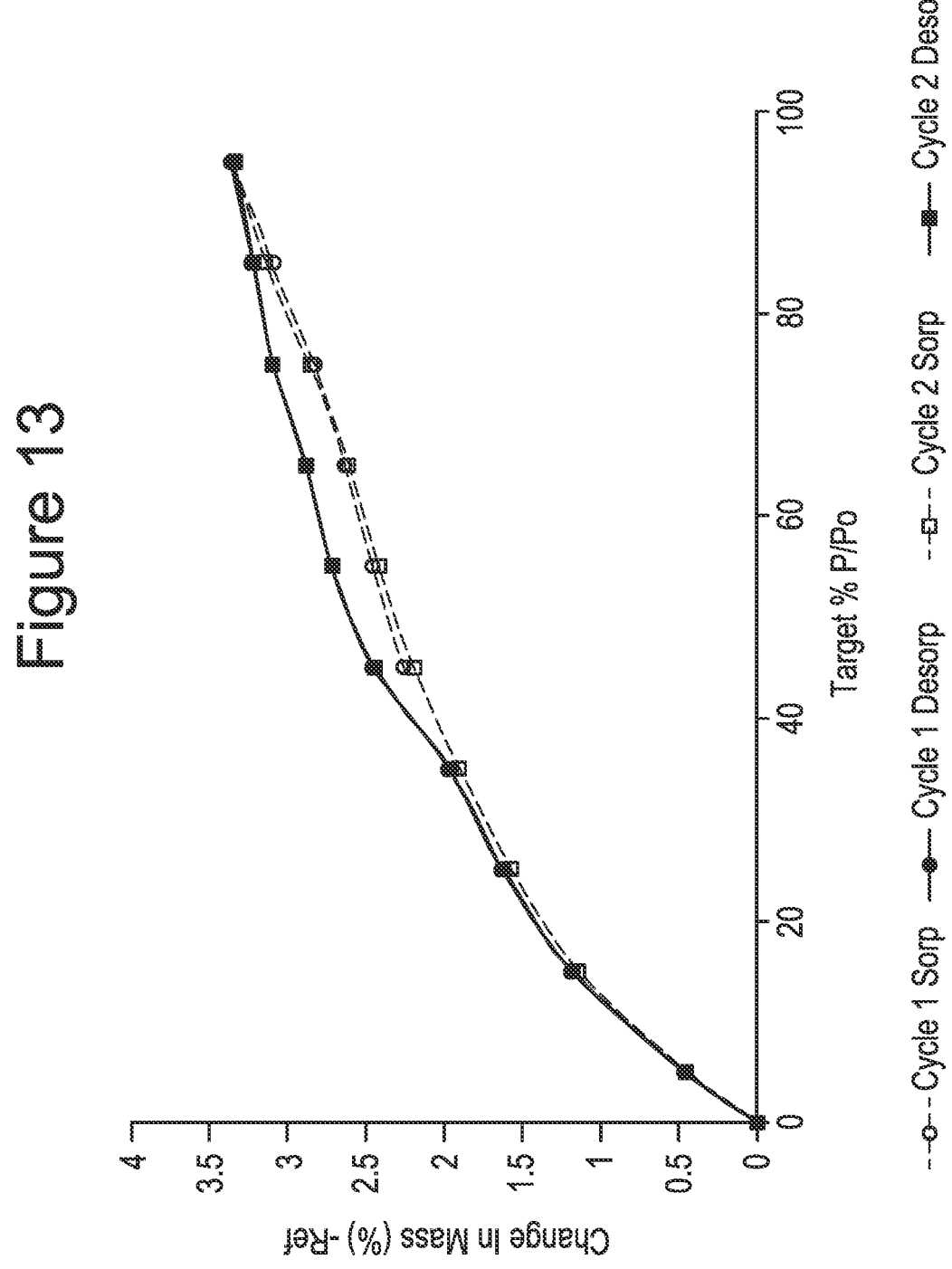
FIG. 13 depicts a moisture sorption profile of the crystalline hydrate form of AMG 397.

The crystalline hydrate form of AMG 397 can be characterized by a moisture sorption profile. For example, in some embodiments the crystalline hydrate form of AMG 397 is characterized by the moisture sorption profile as shown in FIG. 13, showing a weight gain of 3.3% by 95% RH.

Figure 15:
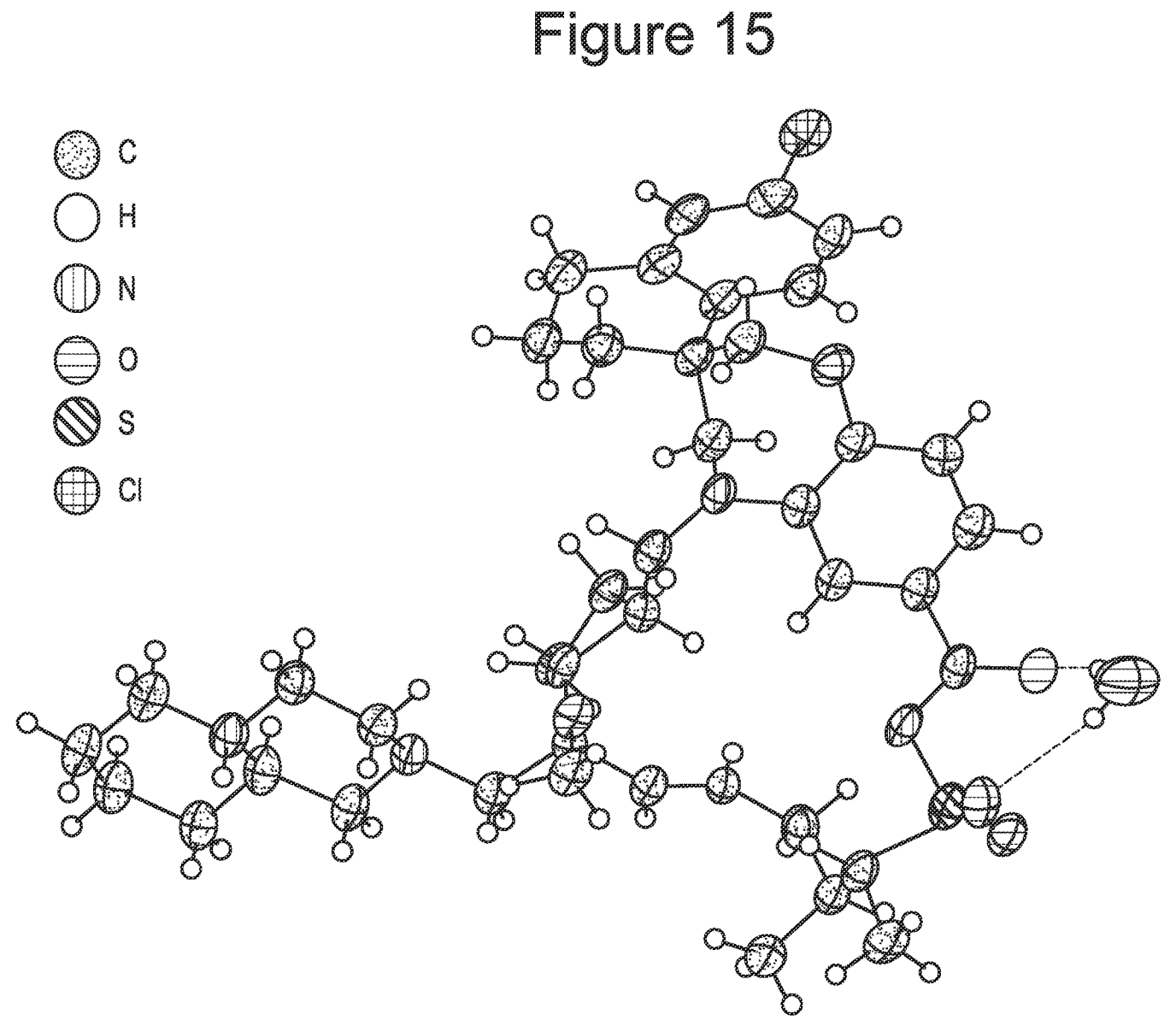

The crystalline hydrate form of AMG 397 is further characterized by a single crystal structure substantially as shown in FIG. 15, or as set forth in the Examples.

Further provided herein are pharmaceutical formulations comprising the crystalline hydrate form of AMG 397 as described herein and a pharmaceutically acceptable excipient. In some embodiments, the pharmaceutical formulation is in the form of a tablet. In some embodiments, the pharmaceutical formulation is in the form of an immediate release tablet.

Methods of Treating a Subject

Further provided herein are methods of treating a subject suffering from cancer, comprising administering to the subject a therapeutically effective amount of a pharmaceutical formulation as disclosed herein. In some embodiments, the cancer is multiple myeloma, non-Hodgkin's lymphoma, or acute myeloid leukemia.

It is to be understood that while the disclosure is read in conjunction with the detailed description thereof, the foregoing description and following example are intended to illustrate and not limit the scope of the disclosure, which is defined by the scope of the appended claims. Other aspects, advantages, and modifications are within the scope of the following claims.

EXAMPLES

Example 1: Preparation of Spray Drying Solution

Solvent selection: The solubility of AMG 397 was measured in solvents commonly used for spray drying. Table 1 shows the solubility results and the properties of each solvent. Based on the solubility data, tetrahydrofuran (THF) was selected as a solvent for the initial spray drying-work and further work was conducted in DCM. The solubility in various ratios of THF-water were also tested as the presence of water has been shown to minimize the residual THF level. The solubility of AMG 397 in THF drops significantly in the presence of water and the concentrations are too low to be considered for spray-drying.

TABLE 1

| | ICH | BP | η | γ | | δ | Solubility |
|---|---|---|---|---|---|---|---|
| Solvent | Limit | (° C.) | (mPa · s) | (mJ/m$^2$) | ε | (cal/cm$^3$) | (mg/ml) |
| Water | N/A | 100.0 | 0.89 | 71.9 | 78.4 | 23.4 | 0.007[2] |
| Methanol | 3000 | 64.7 | 0.54 | 22.1 | 32.6 | 14.5 | 0.09[2] |
| Ethanol | N/A | 78.3 | 1.08 | 22.0 | 24.3 | 12.7 | 0.15[2] |
| Dichloromethane (DCM) | 600 | 39.8 | 0.42 | 27.2 | 8.9 | 9.7 | >100[3] |
| Acetone | Class 3 | 56.3 | 0.30 | 22.7 | 20.7 | 9.6 | 0.37[1] |
| Tetrahydrofuran (THF) | 720 | 66.0 | 0.46 | 26.4 | 7.5 | 9.1 | 33.5[3] |
| Ethyl acetate | Class 3 | 77.1 | 0.43 | 23.2 | 6.0 | 9.0 | 0.75[3] |

The solubility of AMG 39' in THF was initially >50 mg/mL but upon extended stirring at room temperature solid started to precipitate and the final solubility was 33.5 mg/mL after 24 hours. AMG 397 is known to form solvates with many solvents. The formation of a solvate can lead to precipitation from solution due to the lower solubility in the solvent. Care must be taken to select a solvent and concentration of AMG 397 which can be maintained for the duration of the spray-drying process. The solubility of AMG 397 was highest in DCM where concentrations >100 mg/mL were achieved. Both DCM and THF are ICH class II solvents with residual solvent limits of 600 and 720 ppm, respectively. Therefore, the residual solvent levels must be removed to below these levels during the secondary drying process.

The stability of AMG 397 was assessed in both THF and DCM over 24 hours to cover the processing time in the solvent. The stability was assessed in both amber and clear glass vials to assess the impact of light on stability.

The stability data showed that AMG 397 is unstable in THF and the presence of light accelerated degradation. AMG 397 was stable in DCM up to 24 hours at room temperature, however degradation was observed at longer time-points. Light had little impact on degradation up to 72 hours in DCM.

Example 2: Generation and Characterization of Amorphous AMG 397

Before generating solid dispersions of amorphous AMG 397, the amorphous AMG 397 drug substance was prepared using the spray-dryer. This material was used to characterize the amorphous form and used in in vitro and in vivo proof of concept studies.

X-Ray Powder Diffraction: X-ray powder diffraction data were obtained on a PANalytical X'Pert PRO X-ray diffraction system with RTMS detector. Samples were scanned in continuous mode from 5-45° (2θ) with step size of 0.0334°

TABLE 2

Stability of AMG 397 in THF at 1 mg/mL at room temperature

| | | | 2 Hrs | | 4 Hrs | | 24 Hrs | | 72 Hrs | |
|---|---|---|---|---|---|---|---|---|---|---|
| Peak | RRT | Initial | Amber | Clear | Amber | Clear | Amber | Clear | Amber | Clear |
| | | | | | Peak Area % (280 nm) | | | | | |
| AMG 397 | 1.00 | 99.52 | 99.41 | 98.98 | 99.51 | 97.51 | 98.62 | 92.68 | 97.20 | 90.59 |
| | 1.21 | <0.05 | <0.05 | <0.05 | <0.05 | <0.05 | 0.37 | <0.05 | 0.66 | 4.33 |
| | 1.54 | <0.05 | <0.05 | 0.50 | <0.05 | 1.25 | 0.51 | 3.95 | 0.89 | 3.95 |
| | 1.64 | <0.05 | <0.05 | <0.05 | <0.05 | 0.76 | <0.05 | 2.77 | 0.76 | 0.54 |
| | 2.14 | 0.48 | 0.59 | 0.52 | 0.49 | 0.48 | 0.50 | 0.60 | 0.49 | 0.59 |

TABLE 3

Stability of AMG 397 in DCM at 1 mg/mL at room temperature

| | | | 2 Hrs | | 4 Hrs | | 24 Hrs | | 72 Hrs | |
|---|---|---|---|---|---|---|---|---|---|---|
| Peak | RRT | Initial | Amber | Clear | Amber | Amber | Amber | Clear | Amber | Clear |
| | | | | | Peak Area % (280 nm) | | | | | |
| AMG 397 | 1.00 | 99.52 | 99.49 | 99.47 | 99.44 | 99.52 | 99.44 | 99.48 | 99.13 | 98.78 |
| | 0.93 | <0.05 | <0.05 | <0.05 | <0.05 | <0.05 | <0.05 | <0.05 | 0.34 | <0.05 |
| | 1.65 | <0.05 | <0.05 | <0.05 | <0.05 | <0.05 | <0.05 | <0.05 | <0.05 | 0.66 |
| | 2.14 | 0.48 | 0.51 | 0.53 | 0.56 | 0.48 | 0.56 | 0.52 | 0.53 | 0.56 | at 45 kV and 40 mA with CuKα radiation (1.54 Å). The incident beam path was equipped with a 0.02 rad soller slit, 15 mm mask, 4° fixed anti-scatter slit and a programmable divergence slit. The diffracted beam was equipped with a 0.02 rad soller slit, programmable anti-scatter slit and a 0.02 mm nickel filter. Samples were prepared on a low background sample holder and placed on a spinning stage with a rotation time of 2 s. For variable-temperature studies, samples were prepared on a flat plate sample holder and placed in a TTK-450 temperature control stage. For variable-humidity studies, modular humidity generator generator (ProUmid) was used to control atmosphere in THC humidity sample chamber. The XRPD pattern of amorphous AMG 397 material is shown in FIG. 1.

Thermal Analysis: Differential scanning calorimetry (DSC) was performed on a TA Instruments 01000/2000 calorimeter at in an aluminum Tzero pan under dry nitrogen, sant into the vial. Tip over the capped sample several times to ensure suspension and dispersion of the particles (no agglomeration). Rinse the unit system one time with one Acetone wash and followed by two dispersant (heptane +0.5% span 85) washes. Refill the system with dispersant, align the laser and perform the background measurement. Add suspension sample to the unit via a transfer pipette until observed obscuration falls between 10-20%, then start the measurements. The particle size distribution of the amorphous AMG 397 is shown in FIG. 4.

Amorphous AMG 397 material was prepared by dissolving 1031.06 mg of AMG 397 in 52 mL tetrahydrofuran (THF) and shaking to form a yellow solution. The solution was then spray dried at ~2.5 mL/min using the using the operating conditions shown in Table 4. 860 mg of product was collected and dried under vacuum (10 mmHg) oven at 60° C. for 2 days to remove the residual THF.

TABLE 4

| AMG 397 Target Spray Drying Conditions | | | |
|---|---|---|---|
| Material | AMG 397 | Drying gas (kg/min) | 0.50-0.58 |
| Solution Concentration (mg/mL) | 20 | Outlet (° C.) | 52-58 |
| Total amount API (mg) | 2000 | Inlet (° C.) | 60-66 |
| Solvent System | THF w/BHT | Atomizing Air (sL/min) | 6.9-7.1 |
| Solution Concentration (mg/mL) | 20 | Aspirator % | 95-100 |
| Nozzle Cooling (° C.) | 18-22 | System DP (bar) | Less than −0.04 |
| Cyclone Cooling (° C.) | 20-35 | Solution Spray Rate (mL/min) | 2.5 | flowing at 50 ml/min. Thermogravimetric analysis (TGA) was performed on a TA Instruments Q500 analyzer in a platinum pan under dry nitrogen, flowing at 60 mV/min. The DSC and TGA of amorphous AMG is shown in FIG. 2.

Moisture Sorption: Moisture sorption data was collected using a Surface Measurement Systems DVSAdvantage instrument. Equilibrium criteria were set at ±0.001% weight change in 10 minutes with a maximum equilibrium time of 380 minutes. The moisture sorption profile of amorphous AMG 397 is shown in FIG. 3.
Particle Size Distribution:

| Particle Type | Non-Spherical |
|---|---|
| Dispersant (for PSD measurement) | Heptane with 0.5% span 85 (refractive index of 1.387) |
| Dispersant (for Sample Preparation) | Heptane with 0.5% span 85 |
| Background Measurement | 10 seconds |
| Sample Measurement | 10 seconds |
| Number of Measurements During Run | 3 |
| Delay Between Measurements | 10 seconds |
| Pre Measurement Delay | 5 seconds |
| Obscuration Level | 10-20% |
| Stirrer Speed | 3000 rpms |
| Sonication | None |
| Analysis/Calculation Sensitivity | General Purpose (Sensitivity = Normal) |
| Result Type | Volume Distribution |

Weigh 30-100 mg AMG 397 test sample and transfer it to a scintillation vial. Then add approximately 2-5 mL disper- XRPD analysis confirmed that the material was amorphous following spray-drying and did not crystalize following secondary drying (FIG. 1). The dried material was also examined by polarized light microscopy to ensure that no crystallinity remained. The modulated DSC experiment (FIG. 2), performed in a sealed non-hermetic pan heated at 3° C./min with a modulation of +/−0.5° C. every 40 seconds, showed a glass transition (Tg) around 196° C. The corresponding TGA trace (FIG. 2) was obtained by heating a sample at 10° C./min in an open platinum TGA pan under constant nitrogen flow and showed a weight loss of 1.3% associated with the dehydration (water content was 1.6% by karl fisher titration) and a weight loss of 4.9% after passing through the Tg. The moisture sorption profile of amorphous AMG 397 is shown in FIG. 3 and showed a weight gain of ~6.4% by 95% RH.

Additional lots of amorphous AMG 397 were generated by spray-drying using a similar process. The initial amorphous material was used for solid state characterization, physical stability and in vitro dissolution experiments. Lots 1 and 2 were generated to support biopharmaceutical PK studies.

The particle size of four amorphous DS batches were measured using a Horiba laser particle size analyzer. Heptane was used as the dispersant and sample measurements were taken over 10 seconds with a stirrer speed of 3000 rpm. Sample was added to the dispersant until the observed obscuration falls between 10-20%. The results are summarized in FIG. 4 and Table 5.

TABLE 5

| | Particle Size Distribution Data for Amorphous AMG 397 generated by Spray drying | | |
| --- | --- | --- | --- |
| Batch | Particle Size (μm) | | |
| # | D10 | D50 | D90 |
| 1 | 1.40 | 2.85 | 5.36 |
| 2 | 1.54 | 2.67 | 4.79 |
| 3 | 1.52 | 2.12 | 2.84 |
| 4 | 1.45 | 2.28 | 3.26 |

The amorphous drug substance had an almost monodisperse particle size with D50 values <3 μm. As the outlet temperature of the spray-dryer decreased the D50 and span increase.

Example 3: In Vitro Comparison of Amorphous and Crystalline Hydrate AMG 397

Figure 5:
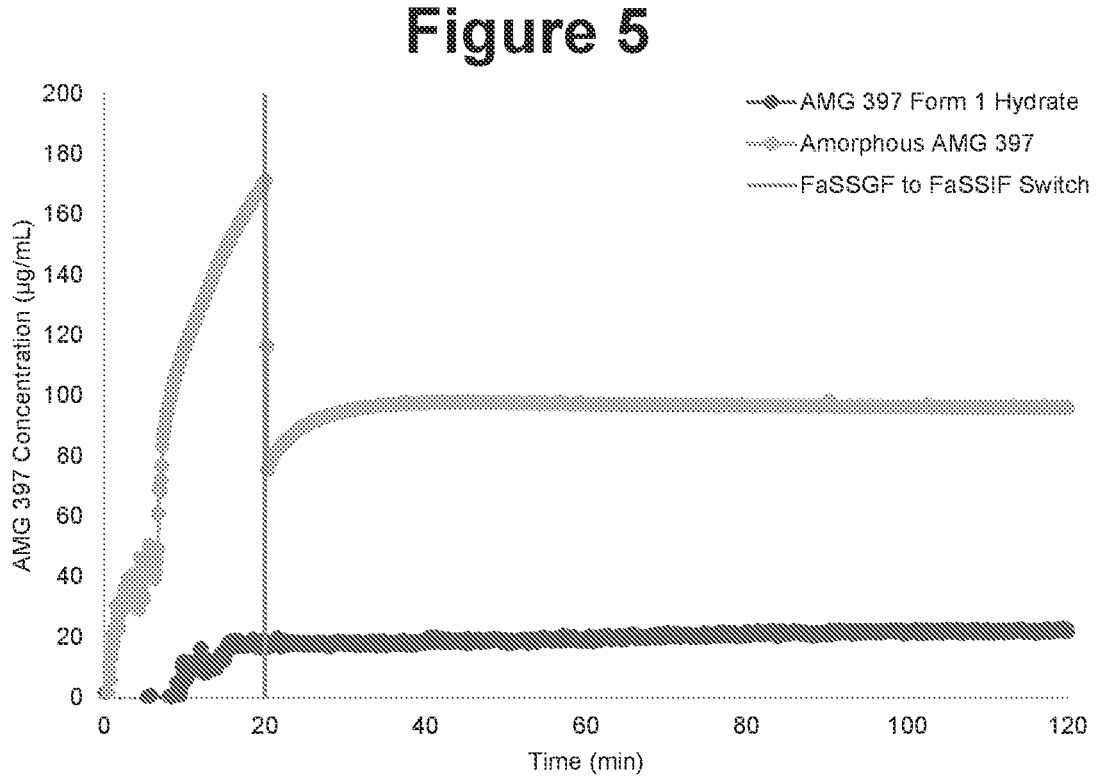
FIG. 5 depicts a graph of a two-stage micro-dissolution comparing the amorphous form of AMG 397 and the crystalline hydrate form of AMG 397.
Figure 6:
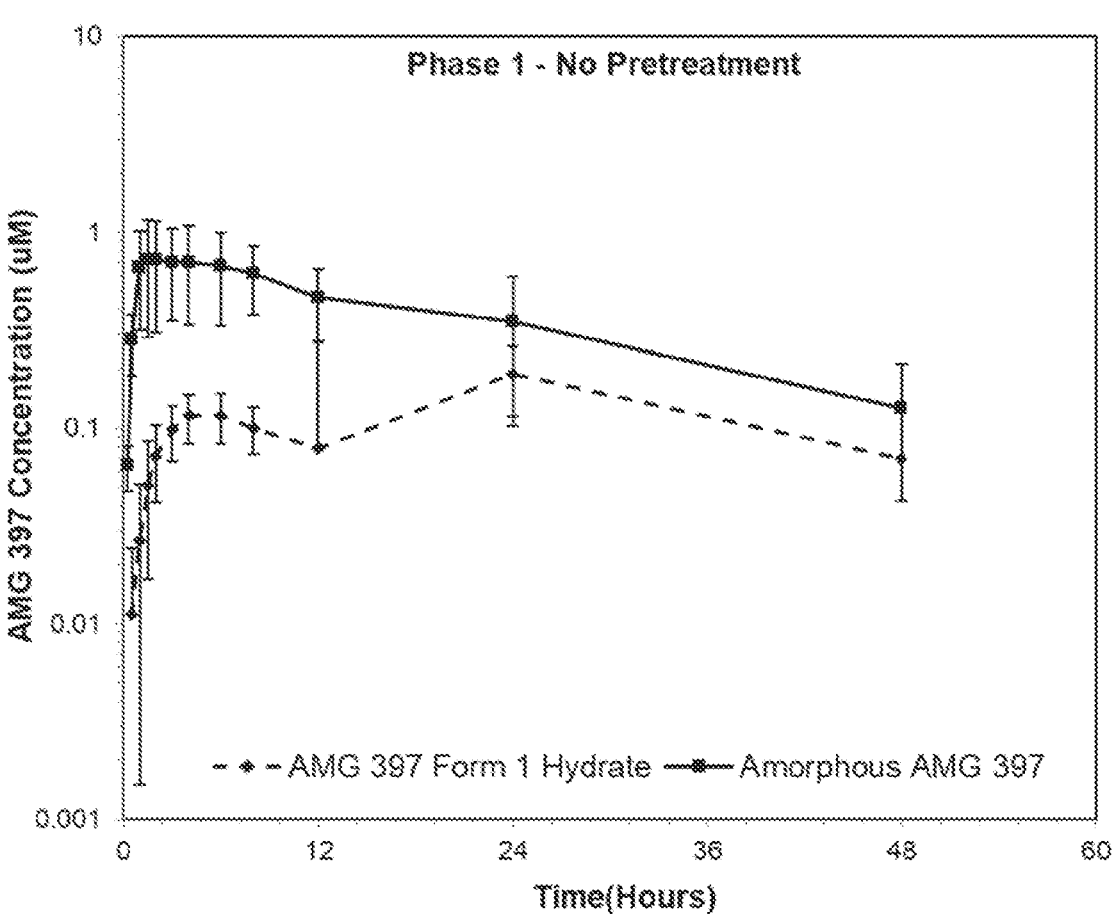
FIG. 6 depicts a graph of the plasma concentrations following oral administration of the solid dispersion and the crystalline hydrate form of AMG 397 to male beagle dogs at 3 mg/kg with no-pretreatment.
Figure 7:
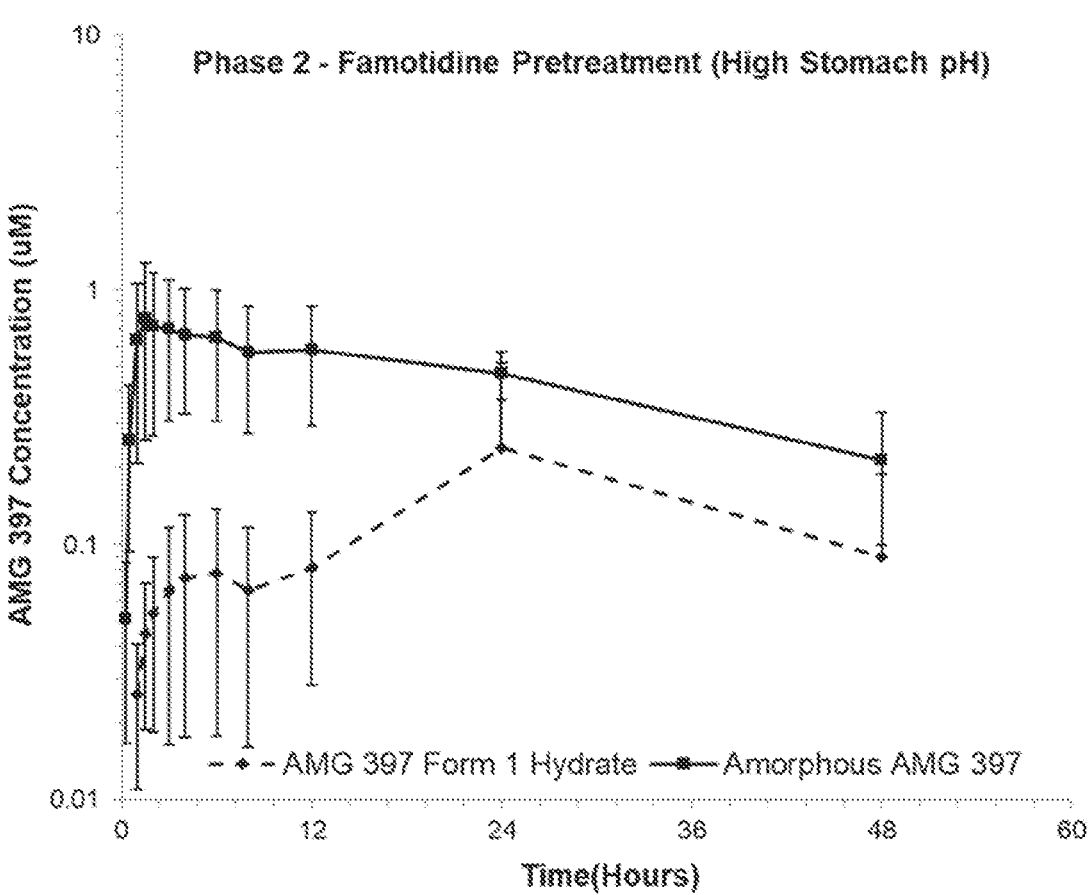
FIG. 7 depicts a graph of the plasma concentrations following oral administration of the solid dispersion and the crystalline hydrate form of AMG 397 to male beagle dogs with high stomach pH at 3 mg/kg with a Famotidine pretreatment.
Figure 8:
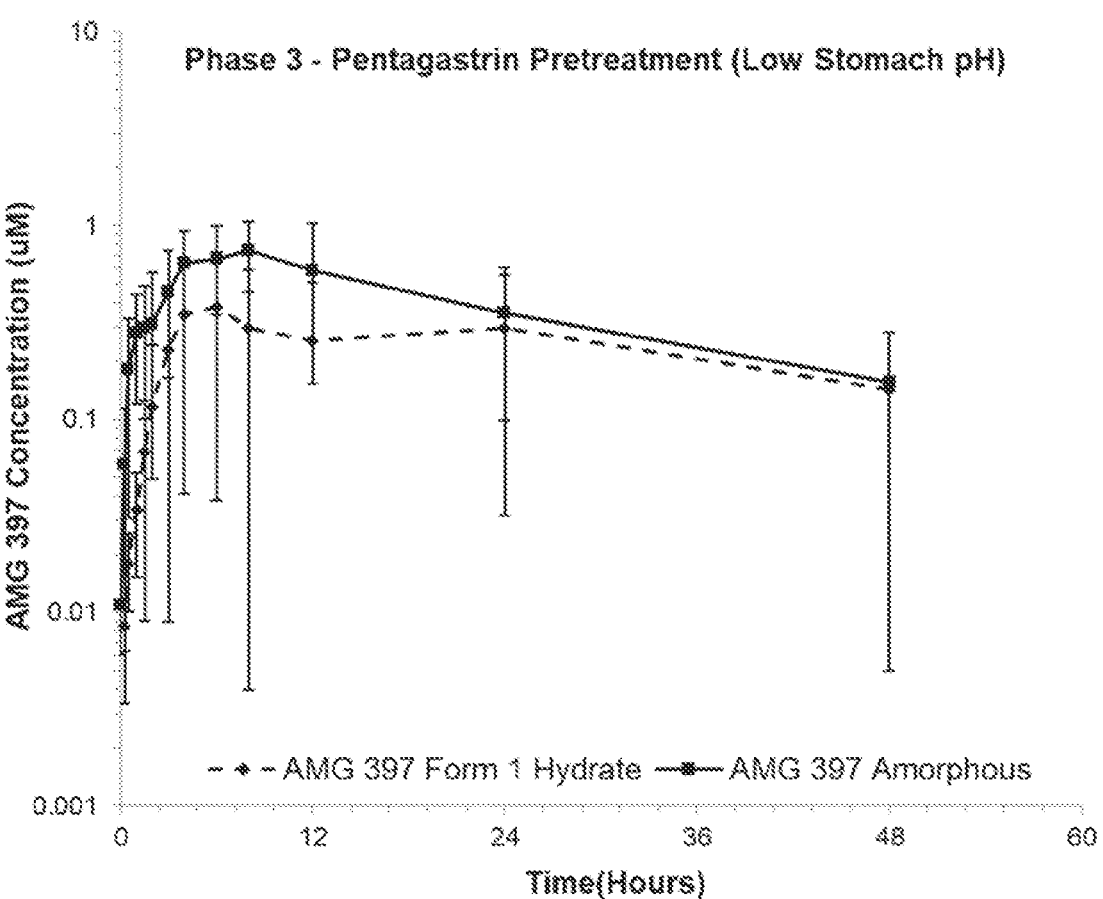
FIG. 8 depicts a graph of the plasma concentrations following oral administration of the solid dispersion and the crystalline hydrate form of AMG 397 to male beagle dogs with low stomach pH at 3 mg/kg with a Pentagastrin pretreatment.
Figure 9:
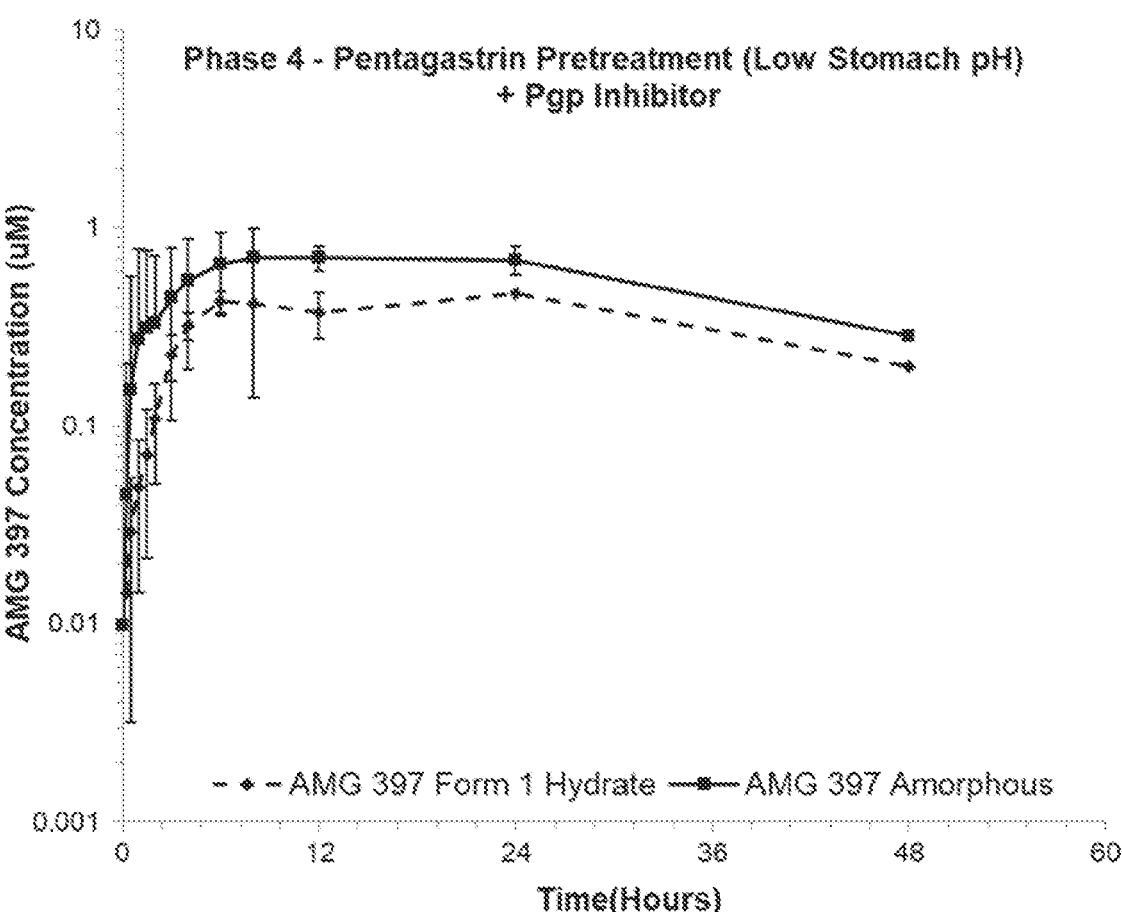
FIG. 9 depicts a graph of the plasma concentrations following oral administration of the solid dispersion and the crystalline hydrate form of AMG 397 to male beagle dogs with low stomach pH at 3 mg/kg with a Pentagastrin pretreatment and a Pgp inhibitor.

A 2-stage micro-dissolution experiment was performed to compare the dissolution of the amorphous AMG 397 drug substance to the crystalline hydrate form of AMG 397, as shown in FIG. 5. The dissolution of Amorphous AMG 397 in simulated gastric fluid (faSSGF) was significantly faster than the crystalline hydrate form of AMG 397 and after 20 minutes the concentration was ~8× higher. Upon dilution with fasted simulated intestinal fluid (faSSIF, pH 6.0 after dilution) the concentration of the amorphous material was seen to drop before increasing over the next 10 minutes and reaching a plateau. No precipitation of the amorphous material was observed, and it maintained at 5× higher concentration than the crystalline hydrate form of AMG 397 for the duration of the experiment. Dissolution of the crystalline hydrate form of AMG 397 was significantly slower, and the concentration achieved in the faSSGF compartment was maintained for the duration of the experiment. Unlike the amorphous material no further dissolution occurred once the media was switched to faSSIF. The dissolution data suggested that an amorphous formulation with precipitation inhibition could be used to enhance the exposure of AMG 397.

Example 4: In Vivo Comparison of Amorphous and Crystalline Hydrate AMG 397

The pharmacokinetics of AMG 397 were assessed following oral administration to male beagle dogs as either a suspension of the crystalline hydrate form of AMG 397 or an amorphous suspension in 2% HPMC, 0.01% Tween 80. The full protocol is described in Amgen study number 150528. The goal of this study was to determine if the amorphous material would lead to increases in bioavailability and if variability in dosing could be reduced. In addition, oncology patients could be receiving acid-reducing agents as co-medication, so it is important to determine if exposure is reduced with elevated stomach pH and if an amorphous formulation of AMG 397 could overcome the drug-drug interaction (DDI). For the studies below, Form 1 is the crystalline hydrate form of AMG 397 and amorphous is the amorphous form of AMG 397.

Briefly, during each phase five male beagle dogs were assigned to each group of the study. All animals were fasted for at least eight hours prior to dosing and through the first four hours of blood sample collection for each phase. Food was returned within 30 minutes following collection of the last blood sample at the four-hour collection interval. Each animal in Phase 1, received a single oral (PO) gavage dose of the appropriate test article formulation as outlined in the study design Table 6. Oral gavage dosing formulations were continuously stirred throughout dosing. The gavage tube was rinsed with approximately 10 mL of tap water following dosing (prior to removal of the gavage tube). Following each study phase a 7-day washout period was allowed prior to the dosing of the next phase. The same five dogs were assigned to either group 1 or group 2 formulations for the duration of the study.

Additional Study Details: The following details represent the standard study conditions/methods. Applicable SOP references may be found in the most recent animal care and use proposal for this species on file with the Institutional Animal Care and Use Committee (IACUC).

Source and Disposition: Animals used on study were transferred from an MPI Research stock colony (999-885) of non-naïve beagle dogs. Original source/health records are on file at MPI Research. All animals were to the stock colony following completion of the study.

Number, Body Weight, and Age: This study was designed to use the fewest number of animals possible, consistent with the objective of the study, the scientific needs of the Sponsor, and contemporary scientific standards. The animals will weigh between approximately 6-16 kg. The actual range may vary but will be documented in the data. Animals that are at least five months of age will be maintained for use. The actual ages of the animals will be maintained in the stock colony records.

Method of Identification: Each animal were assigned an animal number to be used in Provantis™ and were implanted with a microchip bearing a unique identification number. Each animal had a permanent tattoo of a vendor animal number on an earflap. The individual animal number, implant number and/or tattoo, and the MPI Research study number comprised a unique identification for each animal.

Acclimation, Selection, and Randomization: All animals had been previously acclimated at MPI Research. Only healthy animals had been selected for study. No randomization was necessary.

Husbandry: Animals were individually housed in stainless steel cages (with stainless steel or plastic coated flooring) or runs following each dose. If applicable, following the initial 24 hours of sample collection and observation, the animals were socially housed (provided each animal has a suitable cage-mate), unless individual housing is required for study functions such as urine collection. Animals were individually housed for a duration longer than one week following each dose. If required, the dogs were provided the opportunity for exercise a minimum of 30 continuous minutes, three times a week according to SOP. However, animals on study (and neighboring stock colony animals, if applicable) were exercised on dosing days, unless the Study Director is consulted and indicates that this is acceptable. Fluorescent lighting was provided via an automatic timer for approximately 12 hours per day. On occasion, the dark cycle was briefly interrupted to allow for study functions that occur during the 12-hour dark cycle. Food (Lab Diet☐ Certified Canine Diet #5007 [PMI Nutrition International]) was offered according to a meal feeding schedule per SOP except during fasting or restraint periods, where applicable. Water was available ad libitum except during restraint periods, where applicable. Temperature and humidity was maintained as described in SOP. Routine feed/water analysis results were kept on file at MPI Research; no contaminants were present in food or water which would affect the outcome of the study. It may be necessary during the course of the study to offer supplemental food as part of standard veterinary care. This will not be certified diet, but will be commercially available food that has been analyzed for nutritional value. The Study Director is not aware of any contaminants in the supplemental food that may impact the results of the study.

Test Article Analyses and Preparation: The Sponsor assumed responsibility for documenting the characteristics and results of analysis of the bulk test article(s) as well as the homogeneity, stability, and/or concentration of the dosing formulation(s), where applicable. If necessary, pre-formulated dosing formulations were transferred into an appropriate container to facilitate dosing.

Catheterizations: A peripheral vein mat be catheterized for intravenous dosing using standard procedures.

Restraint: For intravenous dosing, previously-acclimated animals may be placed in slings for up to eight hours. At the end of restraint, catheters will be removed and the animals will be returned to their cages where urine collection will begin (if required).

TABLE 6

| Test Article Preparation Details | |
| --- | --- |
| AMG 397<br>Phase 1<br>(Groups 1 and 2) | Vehicle: 0.01% Tween ® 80, 2%<br>hydroxypropylmethylcellulose<br>in deionized water<br>Final Appearance: Opaque, uniform liquids |

TABLE 6-continued

| Test Article Preparation Details | |
| --- | --- |
| AMG 397$^a$<br>Phase 2<br>(Groups 1 and 2) | Vehicle: 0.01% Tween ® 80, 2%<br>hydroxypropylmethylcellulose<br>in deionized water<br>Final Appearance: Opaque, uniform liquids |
| AMG 397$^a$<br>Phase 3<br>(Groups 1 and 2) | Vehicle: 0.01% Tween ® 80, 2%<br>hydroxypropylmethylcellulose<br>in deionized water<br>Final Appearance: Opaque, uniform liquids |
| AMG 397$^a$<br>Phase 4<br>(Groups 1 and 2) | Vehicle: 0.01% Tween ® 80, 2%<br>hydroxypropylmethylcellulose<br>in deionized water<br>Final Appearance: Opaque, uniformed liquids |
| GF120918 Inhibitor<br>Phase 4<br>(Groups 1 and 2) | Final Appearance: Opaque, yellow, uniform<br>suspension |
| AMG 397$^a$<br>Phase 5<br>(Groups 1 and 2) | Vehicle: 0.01% Tween ® 80, 2%<br>hydroxypropylmethylcellulose<br>in deionized water<br>Final Appearance: Opaque, homogenous<br>liquids |
| GF120918 Inhibitor<br>Phase 5<br>(Groups 1 and 2) | Final Appearance: Opaque, homogenous<br>liquid |

$^a$Form 1 (Group 1) and Amorphous (Group 2)

TABLE 7

Dose Administration Details

AMG 397 Form 1 (Oral Gavage)
Phase 1
No Pre-Treatment

| Animal<br>Number | Group<br>Number | Sex | Body<br>Weight<br>(kg) | Dose<br>Level<br>(mg/kg) | Dose<br>Volume<br>(mL/kg) | Dose<br>Concentration<br>(mg/mL) | Volume<br>Administered<br>(mL) |
| --- | --- | --- | --- | --- | --- | --- | --- |
| 1001 | 1 | Male | 9.70 | 3 | 5 | 0.6 | 48.5 |
| 1002 | 1 | Male | 11.80 | 3 | 5 | 0.6 | 59.0 |
| 1003 | 1 | Male | 12.70 | 3 | 5 | 0.6 | 63.5$^a$ |
| 1004 | 1 | Male | 8.50 | 3 | 5 | 0.6 | 42.5 |
| 1005 | 1 | Male | 10.20 | 3 | 5 | 0.6 | 51.0 |

$^a$Small amount of dosing formulation came out of the gavage tube.

AMG 397 Form Amorphous (Oral Gavage)
Phase 1
No Pre-Treatment

| Animal<br>Number | Group<br>Number | Sex | Body<br>Weight<br>(kg) | Dose<br>Level<br>(mg/kg) | Dose<br>Volume<br>(mL/kg) | Dose<br>Concentration<br>(mg/mL) | Volume<br>Administered<br>(mL) |
| --- | --- | --- | --- | --- | --- | --- | --- |
| 2001 | 2 | Male | 9.60 | 3 | 5 | 0.6 | 48.0 |
| 2002 | 2 | Male | 7.80 | 3 | 5 | 0.6 | 39.0 |
| 2003 | 2 | Male | 10.40 | 3 | 5 | 0.6 | 52.0 |
| 2004 | 2 | Male | 10.35 | 3 | 5 | 0.6 | 51.8 |
| 2005 | 2 | Male | 13.05 | 3 | 5 | 0.6 | 65.3 |

AMG 397 Form 1 (Oral Gavage)
Phase 2
Famotidine Pre-Treatment

| Animal<br>Number | Group<br>Numbe | Sex | Body<br>Weight<br>(kg) | Dose<br>Level<br>(mg/kg) | Dose<br>Volume<br>(mL/kg) | Dose<br>Concentration<br>(mg/mL) | Volume<br>Administered<br>(mL) |
| --- | --- | --- | --- | --- | --- | --- | --- |
| 1001 | 1 | Male | 9.50 | 3 | 5 | 0.6 | 47.5 |
| 1002 | 1 | Male | 11.40 | 3 | 5 | 0.6 | 57.0 |
| 1003 | 1 | Male | 12.45 | 3 | 5 | 0.6 | 62.3 |
| 1004 | 1 | Male | 8.45 | 3 | 5 | 0.6 | 42.3 |
| 1005 | 1 | Male | 10.10 | 3 | 5 | 0.6 | 50.5 |

TABLE 7-continued

| Dose Administration Details | | | | | | | |
| --- | --- | --- | --- | --- | --- | --- | --- |

AMG 397 Amorphous (Oral Gavage)
Phase 2
Famotidine Pre-Treatment

| Animal Number | Group Number | Sex | Body Weight (kg) | Dose Level (mg/kg) | Dose Volume (mL/kg) | Dose Concentration (mg/mL) | Volume Administered (mL) |
| --- | --- | --- | --- | --- | --- | --- | --- |
| 2001 | 2 | Male | 9.85 | 3 | 5 | 0.6 | 49.3 |
| 2002 | 2 | Male | 7.70 | 3 | 5 | 0.6 | 38.5 |
| 2003 | 2 | Male | 9.75 | 3 | 5 | 0.6 | 48.8 |
| 2004 | 2 | Male | 10.45 | 3 | 5 | 0.6 | 52.3 |
| 2005 | 2 | Male | 12.95 | 3 | 5 | 0.6 | 64.8 |

AMG 397 Form I (Oral Gavage)
Phase 3
Pentagastrin Pre-Treatment

| Animal Number | Group Number | Sex | Body Weight (kg) | Dose Level (mg/kg) | Dose Volume (mL/kg) | Dose Concentration (mg/mL) | Volume Administered (mL) |
| --- | --- | --- | --- | --- | --- | --- | --- |
| 1001 | 1 | Male | 9.55 | 3 | 5 | 0.6 | 47.8 |
| 1002 | 1 | Male | 11.40 | 3 | 5 | 0.6 | 57.0 |
| 1003 | 1 | Male | 12.20 | 3 | 5 | 0.6 | 61.0 |
| 1004 | 1 | Male | 8.30 | 3 | 5 | 0.6 | 41.5 |
| 1005 | 1 | Male | 10.40 | 3 | 5 | 0.6 | 52.0 |

AMG 397 Amorphous (Oral Gavage)
Phase 3
Pentagastrin Pre-Treatment

| Animal Number | Group Number | Sex | Body Weight (kg) | Dose Level (mg/kg) | Dose Volume (mL/kg) | Dose Concentration (mg/mL) | Volume Administered (mL) |
| --- | --- | --- | --- | --- | --- | --- | --- |
| 2001 | 2 | Male | 9.85 | 3 | 5 | 0.6 | 49.3 |
| 2002 | 2 | Male | 7.85 | 3 | 5 | 0.6 | 39.3 |
| 2003 | 2 | Male | 10.15 | 3 | 5 | 0.6 | 50.8 |
| 2004 | 2 | Male | 10.60 | 3 | 5 | 0.6 | 53.0 |
| 2005 | 2 | Male | 13.15 | 3 | 5 | 0.6 | 65.8 |

AMG 397 Form 1 (Oral Gavage)
Phase 4
Pentagastrin Pre-Treatment and Inhibitor Pre- and Post-Treatment[a]

| Animal Number | Group Number | Sex | Body Weight (kg) | Does Level (mg/kg) | Dose Volume (mL/kg) | Does Concentration (mg/mL) | Volume Administered (mL) |
| --- | --- | --- | --- | --- | --- | --- | --- |
| 1001 | 1 | Male | 9.65 | 3 | 5 | 0.6 | 48.3 |
| 1002 | 1 | Male | 11.35 | 3 | 5 | 0.6 | 56.8 |
| 1003 | 1 | Male | 12.15 | 3 | 5 | 0.6 | 60.8 |
| 1004 | 1 | Male | 8.75 | 3 | 5 | 0.6 | 43.8 |
| 1005 | 1 | Male | 10.30 | 3 | 5 | 0.6 | 51.5 |

AMG 397 Amorphous (Oral Gavage)
Phase 4
Pentagastrin Pre-Treatment and Inhibitor Pre- and Post-Treatment[a]

| Animal Number | Group Number | Sex | Body Weight (kg) | Does Level (mg/kg) | Dose Volume (mL/kg) | Does Concentration (mg/mL) | Volume Administered (mL) |
| --- | --- | --- | --- | --- | --- | --- | --- |
| 2001 | 2 | Male | 9.80 | 3 | 5 | 0.6 | 49.0 |
| 2002 | 2 | Male | 8.20 | 3 | 5 | 0.6 | 41.0 |
| 2003 | 2 | Male | 10.05 | 3 | 5 | 0.6 | 50.3 |
| 2004 | 2 | Male | 10.75 | 3 | 5 | 0.6 | 53.8 |
| 2005 | 2 | Male | 13.25 | 3 | 5 | 0.6 | 66.3 |

TABLE 7-continued

Dose Administration Details

AMG 397 Form 1 (Oral Gavage)
Phase 5 (May 14, 2018)
Inhibitor Pre- and Post-Treatment[a]

| Animal Number | Group Number | Sex | Body Weight (kg) | Does Level (mg/kg) | Dose Volume (mL/kg) | Does Concentration (mg/mL) | Volume Administered (mL) |
|---|---|---|---|---|---|---|---|
| 1001 | 1 | Male | 10.00 | 3 | 5 | 0.6 | 50.0 |
| 1002 | 1 | Male | 11.55 | 3 | 5 | 0.6 | 57.8 |
| 1003 | 1 | Male | 13.0 | 3 | 5 | 0.6 | 65.0 |
| 1004 | 1 | Male | 9.05 | 3 | 5 | 0.6 | 45.3 |
| 1005 | 1 | Male | 9.75 | 3 | 5 | 0.6 | 48.8 |

AMG 397 Amporphous (Oral Gavage)
Phase 5 (May 14, 2018)
Inhibitor Pre- and Post-Treatment[a]

| Animal Number | Group Number | Sex | Body Weight (kg) | Does Level (mg/kg) | Dose Volume (mL/kg) | Does Concentration (mg/mL) | Volume Administered (mL) |
|---|---|---|---|---|---|---|---|
| 2001 | 2 | Male | 9.80 | 3 | 5 | 0.6 | 49.0 |
| 2002 | 2 | Male | 8.65 | 3 | 5 | 0.6 | 43.3 |
| 2003 | 2 | Male | 10.40 | 3 | 5 | 0.6 | 52.0 |
| 2004 | 2 | Male | 10.80 | 3 | 5 | 0.6 | 54.0 |
| 2005 | 2 | Male | 13.75 | 3 | 5 | 0.6 | 68.8 |

[a]Inhibitor pre- and post-treatment was administered to the first four animals only.

TABLE 8

Clinical Observations

Positive Clinical Findings
Phase 1 (Days 1 to 7)

| Animal Number | Group Number | Sex | Dose Time[a] | Observation | Time/Interval Recorded[a] |
|---|---|---|---|---|---|
| 2005 | 2 | Male | Day 1: 10:10 | Yellow, frothy vomitus | Day 1: 10:24 |

Positive Clinical Findings
Phase 2 (Days 8 to 14)

| Animal Number | Group Number | Sex | Dose Time[a] | Observation | Time/Interval Recorded[a] |
|---|---|---|---|---|---|
| 1003 | 1 | Male | Day 8: 10:02 | Limb function impaired (right hind limb) | Day 14: 07:36 |
| 2001 | 2 | Male | Day 8: 10:05 | White, frothy vomitus | Day 8: 14:09 |
| 2003 | 2 | Male | Day 8: 10:07 | Soft feces | Day 8: 12:09 |
| 2004 | 2 | Male | Day 8: 10:08 | White, frothy vomitus | Day 8: 14:09 |
| 2005 | 2 | Male | Day 8: 10:10 | Yellow, frothy vomitus | Day 8: 10:25 |

Positive Clinical Findings
Phase 3 (Days 15 to 21)

| Animal Number | Group Number | Sex | Dose | Time[a] | Time/Interval Recorded[a] |
|---|---|---|---|---|---|
| 1002 | 1 | Male | Day 15: 10:01 | White, frothy vomitus | Day 15: 10:25 |
| 1003 | 1 | Male | Day 15: 10:02 | Limb function impaired (right hind limb) | Day 15: 11:34 and Day 17: 10:34 |
| 1005 | 1 | Male | Day 15: 10:04 | Wet hair on entire body Inappetence | Day 15: 16:09 Day 15: 16:09 |
| 2001 | 2 | Male | Day 15: 10:06 | Salivation | Day 15: 10:22 |
| 2002 | 2 | Male | Day 15: 10:07 | White, frothy vomitus | Day 15: 10:25 |
| 2005 | 2 | Male | Day 15: 10:10 | Yellow, frothy vomitus | Day 15: 10:24 |

TABLE 8-continued

| Clinical Observations |
| --- |

| Positive Clinical Findings<br>Phase 4 (Days 22 to 24) | | | | | |
| --- | --- | --- | --- | --- | --- |
| Animal<br>Number | Group<br>Number | Sex | Dose<br>Time$^a$ | Observation | Time/Interval<br>Recorded$^a$ |
| 1001 | 1 | Male | Day 22: 10:28 | Large amount of white,<br>frothy emesis | Day 22: 11:11 |
| 2002 | 2 | Male | Day 22: 10:37 | Small amount of white,<br>frothy vomitus | Day 22: 11:08 |

| Positive Clinical Findings<br>Phase 5 (Days 71 to 73) | | | | | |
| --- | --- | --- | --- | --- | --- |
| Animal<br>Number | Group<br>Number | Sex | Dose<br>Time$^a$ | Observation | Time/Interval<br>Recorded$^a$ |
| 2001 | 2 | Male | Day 71: 10:26 | Salivation | Day 71: 14:29 |
| 2004 | 2 | Male | Day 71: 10:30 | Watery feces | Day 71: 14:37 and<br>16:25 |
|  |  |  |  | Yellow, frothy vomitus | Day 71: 14:37 |
|  |  |  |  | Yellow, discolored feces | Day 71: 16:25 |
|  |  |  |  | Mucoid feces | Day 71: 16:25 |
| 2005 | 2 | Male | Day 71: 10:32 | Tan, frothy vomitus | Day 71: 10:46 |

$^a$24-hour clock

Test Article Administration: A total of 10 male beagle dogs were initially assigned to study. All animals were fasted for at least eight hours prior to dosing and through the first four hours of blood sample collection for each phase, where applicable (food will be returned within 30 minutes following collection of the last blood sample at the four hour collection interval, where applicable). Total fasting time did exceed 24 hours.

Each animal in Phase 1, Groups 1 and 2 received a single oral (PO) gavage dose of the appropriate test article formulation as outlined in the following study design table. Oral gavage dosing formulations was continuously stirred throughout dosing. The gavage tube was rinsed with approximately 10 mL of tap water following dosing (prior to removal of the gavage tube). No pre-treatment will be required for Phase 1.

After a 7-day washout period, each animal in Phase 2, Groups 1and 2 received a single oral (PO) gavage dose of the appropriate test article formulation as outlined in the following study design table. Oral gavage dosing formulations were continuously stirred throughout dosing. The gavage tube were rinsed with approximately 10 mL of tap water following dosing (prior to removal of the gavage tube). Two hours prior to dosing, each animal received two 20 mg (40 mg total) oral tablets of famotidine followed by a 10 mL dose of deionized water.

After another 7-day washout period, each animal in Phase 3, Groups 1and 2 received a single oral (PO) gavage dose of the appropriate test article formulation as outlined in the following study design table. Oral gavage dosing formulations were continuously stirred throughout dosing. The gavage tube was rinsed with approximately 10 mL of tap water following dosing (prior to removal of the gavage tube). Thirty minutes prior to dosing, each animal received an intramuscular dose of pentagastrin in phosphate buffered saline at a dose level of 0.006 mg/kg and a dose volume of 0.05 mL/kg.

After a final 7-day washout period, each animal in Phase 4, Groups 1 and 2 received a single oral (PO) gavage dose of the appropriate test article formulation as outlined in the following study design table. Oral gavage dosing formulations were continuously stirred throughout dosing. The gavage tube was rinsed with approximately 10 mL of tap water following dosing (prior to removal of the gavage tube). Thirty minutes prior to dosing, each animal received an intramuscular dose of pentagastrin in phosphate buffered saline at a dose level of 0.006 mg/kg and a dose volume of 0.05 mL/kg plus an additional inhibitor to be added by amendment.

TABLE 9

| Crystalline Hydrate & Amorphous AMG 397 Dog PK Study Design | | | | | | | |
| --- | --- | --- | --- | --- | --- | --- | --- |
| Group | Test<br>Article | Number<br>of Males | Dose<br>Route | Vehicle | Dose Level<br>(mg/kg) | Dose Volume<br>(mL/kg) | Collection<br>Intervals |
| Phase 1 (No pre-treatment) | | | | | | | |
| 1 | AMG 397<br>Form 1 | 5 | PO | A | 3 | 5 | Blood$^B$ |
| 2 | AMG 397<br>amorphous | 5 | PO | A | 3 | 5 | Blood$^B$ |
| Phase 2 (pre-treatment with famotidine -<br>two 20 mg tablets, 2 hour pre-dose) | | | | | | | |
| 1 | AMG 397<br>Form 1 | 5 | PO | A | 3 | 5 | Blood$^B$ |
| 2 | AMG 397<br>amorphous | 5 | PO | A | 3 | 5 | Blood$^B$ |

TABLE 9-continued

| | | | | | Crystalline Hydrate & Amorphous AMG 397 Dog PK Study Design | | |
|---|---|---|---|---|---|---|---|
| Group | Test Article | Number of Males | Dose Route | Vehicle | Dose Level (mg/kg) | Dose Volume (mL/kg) | Collection Intervals |
| | | Phase 3 (pre-treatment with pentagastrin - 6 μg/kg IM, 30 minutes pre-dose) | | | | | |
| 1 | AMG 397 Form 1 | 5 | PO | A | 3 | 5 | Blood[B] |
| 2 | AMG 397 amorphous | 5 | PO | A | 3 | 5 | Blood[B] |
| | | Phase 4 (pre-treatment with pentagastrin - 6 μg/kg IM, 30 minutes pre-dose + GF120913) | | | | | |
| 1 | AMG 397 Form 1 | 5 | PO | A | 3 | 5 | Blood[B] |
| 2 | AMG 397 amorphous | 5 | PO | A | 3 | 5 | Blood[B] |

A 0.01% Tween 80, 2% HPMIC in deionized water
[B]Blood samples will be collected predose and at 0.25 (15 min.), 0.5 (30 min), 1, 1.5, 2. 3, 4, 6, 8, 12, 24, and 48 hours postdose for each phase.

Different pre-treatments were assigned for each phase of the study to mimic several scenarios:

1. No pre-treatment was administered for Phase 1 as it served as a control.
2. During Phase 2, at 1 hour 54 minutes to 1 hour 58 minutes prior to dose administration, all animals were pretreated with two 20 mg (40 mg total) oral tablets of famotidine followed by a 10 mL dose of deionized water. This dose was shown to elevate the stomach pH of dogs to ~pH 6.5. This was used to determine the role of stomach pH on exposure.
3. During Phases 3 and 4, at 30 to 38 minutes prior to dose administration, all animals were pretreated with a single intramuscular dose of pentagastrin in phosphate buffered saline, pH 7.4, at a dose level of 0.006 mg/kg and a dose volume of 0.05 mL/kg. The pentagastrin dose was used to ensure that the dogs stomach pH was normalized to pH ~2.0 as it is known that the dogs stomach pH is often higher than that of humans under resting conditions.
4. In addition, a P-gp inhibitor (GF120918) was also administered in Phase 4, at 1 hour 3 minutes to 1 hour 6 minutes prior to dose administration and 4 hours 10 minutes to 4 hours 11 minutes following dose by oral gavage at a dose level of 3 mg/kg and a dose volume of 4 mL/kg. This final phase was used to study if P-gp played a role in absorption. The pharmacokinetic results are shown in FIGS. 6-9 and summarized in tables 10 & 11.

TABLE 10

Pharmacokinetic results for AMG 397 following oral administration of the crystalline hydrate to male beagle dogs at 3 mg/kg

| | AMG 397 Crystalline Hydrate | | | |
|---|---|---|---|---|
| | Phase 1 | Phase 2 | Phase 3 | Phase 4 |
| AUCt (μM*h) | 5.5 | 6.3 | 11.3 | 16.3 |
| Cl/F (L/h/kg) | 2.5 | 2.6 | 0.83 | 0.31 |
| T½ (h) | 17.3 | 16.5 | 23.3 | 25.0 |
| Cmax (μM) | 0.23 | 0.26 | 0.45 | 0.6 |
| Tmax (h) | 12.4 | 12.8 | 13.2 | 11.6 |
| Relative % F | 1.00 | 1.13 | 2.03 | 2.93 |

TABLE 11

Pharmacokinetic results for amorphous AMG 397 following oral administration to male beagle dogs at 3 mg/kg

| | AMG 397 Amorphous | | | |
|---|---|---|---|---|
| | Phase 1 | Phase 2 | Phase 3 | Phase 4 |
| AUCt (μM*h) | 17.3 | 21.1 | 18 | 26.0 |
| Cl/F (L/h/kg) | 0.4 | 0.22 | 0.26 | 0.26 |
| T½ (h) | 18.4 | 19.7 | 18.3 | 16.5 |
| Cmax (μM) | 0.79 | 0.90 | 0.78 | 0.95 |
| Tmax (h) | 3.1 | 8.1 | 10.4 | 12.4 |
| Relative % F | 1.00 | 1.22 | 1.04 | 1.50 |

The bioavailability of the amorphous material was higher than the crystalline hydrate form under all pretreatment conditions. As no IV arm was included in the study the relative bioavailability numbers are reported for each treatment group compared to Phase 1 of each form. As expected the dogs with no-pretreatment behaved similarly to those with elevated stomach pH. The bioavailability of amorphous AMG 397 was 1.6-fold higher than the crystalline hydrate form when stomach pH was low and 3.4-fold higher when stomach pH was elevated. This difference was driven by the fact that the amorphous material was not affected by stomach pH whereas the crystalline hydrate form had a 2-fold decrease in exposure as stomach pH dropped. Both formulations were equally affected by the addition of a P-gp inhibitor with exposure increasing by 44%.

Example 5: Solid Dispersions Stability Testing

Two AMG 397 amorphous solid dispersions (ASDs) were prepared by spray-drying using THF as the solvent. The polymers used to prepare these dispersions were soluplus and HPMC-AS-LF (Affinisol 716). These polymers were selected as they have been qualified for use by Amgen. The drug:polymer ratio used for the dispersions was 50:50 which is expected to generate a physically stable ASD based on a Tm/Tg ratio of 1.27.

The chemical and physical stability of AMG 397 50% drug load ASDs generated by spray drying from THF was monitored over 4 weeks under accelerated conditions. Chemical stability was measured by HPLC and physical stability by XRPD, DSC and TGA. Samples were stored at 40° C./75% RH open, 40° C./75% RH closed, 25° C./60% RH closed, and 5° C. closed. All samples were tested after storage for 4 weeks except for the 40° C./75% RH open condition that was also tested at weeks 1 and 2. The THF ASD samples had significant degradation at TO due to the use of THF as the spray solvent. Increases in total impurities were observed at 4-weeks under all storage conditions for amorphous AMG 397. The increases in total impurities were correlated with storage at increased temperature and humidity. Unlike the amorphous DS, the ASD samples were stable when stored at 5° C. for 4-weeks. The soluplus ASD also had lower total impurities present after 4 weeks of storage under all conditions compared to the HPMC-AS ASD.

Two further amorphous solid dispersions (ASD) were therefore prepared by spray-drying using DCM as the solvent in place of THF. Soluplus was used to prepare both these dispersions due to its improved stability over HPMC-AS ASDs generated from THF. The spray-drying processing conditions used to generate the ASDs are shown in Table 12. Two drug loads were investigated, 25% and 50%.

TABLE 12

| Spray Drying Conditions used for generating Soluplus ASDs from DCM | | |
| --- | --- | --- |
| Material Lot # | 5 | 6 |
| Total Amount API (mg) | 503.7 | 1002.3 |
| Total Amount Polymer (mg) | 1503.6 | 1003 |
| Solvent System | DCM | DCM |
| Solution Concentration (mg/mL) | 20 | 20 |
| Nozzle Cooling (° C.) | 18-25 | 18-25 |
| Cyclone Cooling (° C.) | 18-25 | 18-25 |

TABLE 12-continued

| Spray Drying Conditions used for generating Soluplus ASDs from DCM | | |
| --- | --- | --- |
| Material Lot # | 5 | 6 |
| Drying gas (kg/min) | 0.50-0.58 | 0.50-0.58 |
| Outlet (° C.) | 45-55 | 45-55 |
| Inlet (° C.) | 60-70 | 60-70 |
| Atomizing Air (sL/min) | 6.9-7.3 | 6.9-7.3 |
| Aspirator % | 90-100 | 90-100 |
| System DP (bar) | <−0.05 | <−0.05 |
| Solution Spray Rate (mL/min) | 2.0 | 2.0 |
| Initial Residual Solvent Level (ppm) | 5932 | 5439 |
| Final Residual Solvent (Post 4 hr Secondary Drying) (ppm) | N.D. | N.D. |
| Wet Yield (%) | 73.3 | 69.17 |

The chemical stability of AMG 397 Soluplus ASDs generated by spray drying using DCM was monitored during each processing step to ensure that no degradation occurred during spray-drying or secondary drying. Samples were also stored for 4 weeks under the following conditions: 5° C. closed, 25° C. closed, 25°,C/60% RH closed, 25° C./60% RH open, 40° C./75% RH open and 40° C./75% RH closed. Residual solvent levels were also tracked during the process. The results are shown in Tables 13-16.

The ASDs generated using DCM as the solvent system were stable through spray-drying and secondary drying. After storage for 4 weeks under accelerated conditions impurity growth was seen under the 40° C./75% RH open and 40° C./75% RH closed conditions. Total impurity levels remained beyond the specification limit of 3.5% and samples were stable when stored under the 5° C. and 25° C. closed conditions.

TABLE 13

| Stability Data for Development Batch of 25:75% w/w AMG 397:Soluplus Spray Dried from DCM | | | | | |
| --- | --- | --- | --- | --- | --- |
| | | | Process Step | | |
| Test | Acceptance Criteria | Initial DS | Post Spray drying | 2-Hr Secondary Drying | 4-Hr Secondary Drying |
| Description | Report | Off-White | Off-White | Off-White | Off-White |
| AMG 397 LCAP (%) | | 98.34 | 98.47 | 98.55 | 98.57 |
| Organic Impurities | | | | | |
| Any single | ≤0.5 | 0.90:0.10 | 0.89:0.09 | 0.89:0.09 | 0.90:0.07 |
| unspecified | | 3170285:0.29 | 3170285:0.38 | 3170285:0.30 | 3170285:0.30 |
| impurity (%) | | 0.98:0.07 | 0.98:0.07 | 0.98:0.07 | 1.16:0.06 |
| | | 1.06:0.06 | 1.15:0.06 | 1.15:0.06 | 1.31:0.07 |
| | | 1.16:0.07 | 1.26:0.06 | 1.26:0.06 | |
| | | 1.32:0.06 | 2.17:0.10 | 2.17:0.09 | |
| | | 2.23:0.08 | | | |
| | | Dimer:0.63 | Dimer:0.64 | Dimer:0.64 | Dimer:0.55 |
| | | 2.30:0.15 | 2.22:0.13 | 2.22:0.14 | 2.42:0.17 |
| | | 2.40:0.08 | | | 2.48:0.13 |
| | | 2.47:0.06 | | | 2.59:0.09 |
| Total impurities (%) | ≤3.5 | 1.66 | 1.53 | 1.45 | 1.43 |
| Residual Solvent DCM | 600 ppm | NT | 5932 | 594 | N.D. |

NT: Not Tested,

N.D.: Not Detected

TABLE 14

Stability Data for Development Batch of 50:50% w/w AMG 397:Soluplus Spray Dried from DCM

| | | | Process Step | | |
|---|---|---|---|---|---|
| Test | Acceptance Criteria | Initial DS | Post Spray drying | 2-Hr Secondary Drying | 4-Hr Secondary Drying |
| Description | Report | Off-White | Off-White | Off-White | Off-White |
| AMG 397 LCAP (%) | | 98.34 | 98.44 | 98.40 | 98.31 |
| Organic Impurities | | | | | |
| Any single unspecified impurity (%) | ≤0.5 | 0.90:0.10 | 0.89:0.08 | 0.89:0.08 | 0.90:0.07 |
| | | 3170285:0.29 | 3170285:0.32 | 3170285:0.33 | 3170285:0.31 |
| | | 0.98:0.07 | 0.98:0.07 | 0.98:0.08 | 1.16:0.06 |
| | | 1.06:0.06 | 1.16:0.06 | 1.16:0.06 | 1.32:0.08 |
| | | 1.16:0.07 | 1.27:0.06 | 1.27:0.07 | |
| | | 1.32:0.06 | 1.81:0.04 | 1.90:0.06 | |
| | | 2.23:0.08 | | 1.91:0.06 | |
| | | Dimer:0.63 | Dimer:0.64 | Dimer:0.62 | Dimer:0.72 |
| | | 2.30:0.15 | 2.17:0.13 | 2.17:0.11 | 2.40:0.20 |
| | | 2.40:0.08 | 2.23:0.15 | 2.23:0.14 | 2.47:0.14 |
| | | 2.47:0.06 | | | 2.59:0.11 |
| Total impurities (%) | ≤3.5 | 1.66 | 1.56 | 1.60 | 1.69 |
| Residual Solvent DCM | 600 ppm | NT | 5439 | 1102 | N.D. |

NT: Not Tested,
N.D.: Not Detected

TABLE 15

Stability Data for Development Batch of 25:75% w/w AMG 397:Soluplus Spray Dried from DCM

| | | | Condition | | |
|---|---|---|---|---|---|
| Test Description | Acceptance Criteria Report | T0 SDD Off-White | 1-Month 5 C. Closed | 1-Month 25 C. Closed | 1-Month 25/60 Closed |
| AMG 397 LCAP (%) | | 98.57 | 98.49 | 98.53 | 98.42 |
| Organic Impurities | | | | | |
| Any single unspecified impurity (%) | ≤0.5 | 0.90:0.07 | 0.89:0.09 | 0.87:0.08 | 0.89:0.08 |
| | | 3170285:0.30 | 3170285:0.29 | 3170285:0.29 | 3170285:0.29 |
| | | | 0.97:0.06 | 0.97:0.06 | 0.97:0.06 |
| | | | 1.05:0.06 | 1.05:0.06 | 1.05:0.06 |
| | | 1.16:0.06 | 1.15:0.06 | 1.15:0.06 | 1.15:0.06 |
| | | 1.31:0.07 | | | 1.25:0.06 |
| | | | 1.30:0.06 | 1.30:0.07 | 1.30:0.08 |
| | | | | | 1.46:0.05 |
| | | | 2.29:0.08 | 2.29:0.07 | 2.29:0.07 |
| | | Dimer:0.55 | Dimer:0.60 | Dimer:0.60 | Dimer:0.60 |
| | | 2.42:0.17 | 2.36:0.11 | 2.36:0.12 | 2.36:0.11 |
| | | 2.48:0.13 | 2.47:0.10 | 2.47:0.08 | 2.47:0.07 |
| | | 2.59:0.09 | | | |
| Total impurities (%) | ≤3.5 | 1.43 | 1.51 | 1.47 | 1.58 |
| Residual Solvent DCM | 600 ppm | N.D. | | | |

| | | Condition | | |
|---|---|---|---|---|
| | Test Description | 1-Month 25/60 Open | 1-Month 40/75 Closed | 1-Month 40/75 Open |
| | AMG 397 LCAP (%) | 98.29 | 98.21 | 97.96 |
| | Organic Impurities | | | |
| | Any single unspecified impurity (%) | 0.89:0.08 | 0.89:0.07 | 0.89:0.05 |
| | | 3170285:0.28 | 3170285:0.29 | 3170285:0.33 |
| | | 0.97:0.05 | 0.97:0.05 | 0.97:0.05 |

TABLE 15-continued

| Stability Data for Development Batch of 25:75% w/w AMG 397:Soluplus Spray Dried from DCM | | | |
|---|---|---|---|
| | 1.05:0.05 | 1.05:0.06 | 1.05:0.12 |
| | 1.15:0.06 | 1.15:0.05 | 1.15:0.11 |
| | 1.25:0.08 | 1.25:0.11 | 1.25:0.22 |
| | 1.30:0.07 | 1.30:0.09 | 1.30:0.07 |
| | 1.46:0.18 | 1.46:0.20 | 1.46:0.15 |
| | | | 3079018:0.05 |
| | 2.30:0.07 | 2.30:0.07 | 2.30:0.07 |
| | Dimer:0.58 | Dimer:0.60 | Dimer:0.59 |
| | 2.37:0.10 | 2.37:0.11 | 2.37:0.11 |
| | 2.47:0.10 | 2.47:0.08 | 2.47:0.08 |
| Total impurities (%) | 1.71 | 1.79 | 2.04 |
| Residual Solvent DCM | | | |

NT: Not Tested,
N.D.: Not Detected

TABLE 16

Stability Data for Development Batch of 50:50%
w/w AMG 397:Soluplus Spray Dried from DCM

| | | | Condition | | |
|---|---|---|---|---|---|
| Test Description | Acceptance Criteria Report | T0 SDD Off-White | 1-Month 5 C. Closed | 1-Month 25 C. Closed | 1-Month 25/60 Closed |
| AMG 397 LCAP (%) | | 98.31 | N.T. | 98.44 | 98.46 |
| Organic Impurities | | | | | |
| Any single unspecified impurity (%) | ≤0.5 | 0.90:0.07 | | 0.89:0.09 | 0.89:0.09 |
| | | 3170285:0.31 | | 3170285:0.31 | 3170285:0.31 |
| | | | | 0.97:0.07 | 0.97:0.07 |
| | | | | 1.05:0.06 | 1.05:0.06 |
| | | | | 1.15:0.06 | 1.15:0.06 |
| | | 1.16:0.06 | | | |
| | | 1.32:0.08 | | 1.31:0.07 | 1.31:0.07 |
| | | | | 2.30:0.08 | 2.30:0.07 |
| | | Dimer:0.72 | | Dimer:0.61 | Dimer:0.61 |
| | | 2.40:0.20 | | 2.37:0.12 | 2.37:0.12 |
| | | 2.47:0.14 | | 2.48:0.09 | 2.48:0.09 |
| | | 2.59:0.11 | | | |
| Total impurities (%) | ≤3.5 | 1.69 | — | 1.56 | 1.54 |
| Residual Solvent DCM | 600 ppm | N.D. | | | |

| | | Condition | | |
|---|---|---|---|---|
| | Test Description | 1-Month 25/60 Open | 1-Month 40/75 Closed | 1-Month 40/75 Open |
| | AMG 397 LCAP (%) | 98.40 | 98.30 | 97.32 |
| | Organic Impurities | | | |
| | Any single unspecified impurity (%) | 0.89:0.08 | 0.89:0.08 | 0.89:0.08 |
| | | 3170285:0.30 | 3170285:0.32 | 3170285:0.38 |
| | | 0.97:0.04 | 0.97:0.06 | 0.97:0.04 |
| | | 1.05:0.05 | 1.05:0.07 | 1.05:0.06 |
| | | | | 3365457:0.05 |
| | | 1.10:0.04 | | 1.10:0.04 |
| | | | | 1.15:0.06 |
| | | 1.16:0.06 | 1.16:0.06 | 1.16:0.07 |
| | | | | 1.18:0.12 |
| | | | | 1.21:0.07 |
| | | | | 1.24:0.27 |
| | | 1.31:0.08 | 1.30:0.08 | 1.30:0.10 |
| | | 1.47:0.11 | 1.45:0.12 | 1.45:0.45 |
| | | 2.31:0.07 | 2.30:0.07 | 2.30:0.08 |

TABLE 16-continued

Stability Data for Development Batch of 50:50%
w/w AMG 397:Soluplus Spray Dried from DCM

| | Dimer:0.59 2.37:0.12 2.48:0.08 | Dimer:0.61 2.37:0.12 2.46:0.09 | Dimer:0.61 2.37:0.12 2.46:0.09 |
|---|---|---|---|
| Total impurities (%) | 1.60 | 1.70 | 2.68 |
| Residual Solvent DCM | | | |

NT: Not Tested,
N.D.: Not Detected

Example 6: Preparation and Characterization of Crystalline Hydrate Form of AMG 397

The crystalline hydrate form of AMG 397 was formed by combining AMG 397 with ~10 volumes of 95:5 ethanol/water. Heat cycled to 70° C. in sealed vial for 15 min then cooled.

X-Ray Powder Diffraction: X-ray powder diffraction data were obtained on a PANalytical X'Pert PRO X-ray diffraction system with RTMS detector. Samples were scanned in continuous mode from 5-45° (2θ) with step size of 0.0334° at 45 kV and 40 mA with CuKα radiation (1.54 Å). The incident beam path was equipped with a 0.02 rad soller slit, 15 mm mask, 4° fixed anti-scatter slit and a programmable divergence slit. The diffracted beam was equipped with a 0.02 rad soller slit, programmable anti-scatter slit and a 0.02 mm nickel filter. Samples were prepared on a low background sample holder and placed on a spinning stage with a rotation time of 2 s. For variable-temperature studies, samples were prepared on a flat plate sample holder and placed in a TTK-450 temperature control stage. For variable-humidity studies, modular humidity generator generator (ProUmid) was used to control atmosphere in THC humidity sample chamber. The XRPD pattern of the crystalline hydrate form of AMG 397 material is shown in FIG. 14.

Thermal Analysis: Differential scanning calorimetry (DSC) was performed on a TA Instruments Q1000/2000 calorimeter at in an aluminum Tzero pan under dry nitrogen, flowing at 50 ml/min. The DSC of the crystalline hydrate form of AMG 397 is shown in FIG. 11. Thermogravimetric analysis (TGA) was performed on a TA Instruments Q500 analyzer in a platinum pan under dry nitrogen, flowing at 60 mi/min. The DSC and TGA of the crystalline hydrate form of AMG 397 is shown in FIG. 12.

Moisture Sorption: Moisture sorption data was collected using a Surface Measurement Systems DVSAdvantage instrument. Equilibrium criteria were set at ±0.001% weight change in 10 minutes with a maximum equilibrium time of 360 minutes. The moisture sorption profile of the crystalline hydrate form of AMG 397 is shown in FIG. 13.

TABLE 17

XRPD Data Table

| Pos. [°2θ] | FWHM [°2θ] | d-spacing [Å] | Height [cts] | Rel. Int. [%] |
|---|---|---|---|---|
| 8.08 | 0.13 | 10.95 | 8694.81 | 13.74 |
| 10.28 | 0.13 | 8.60 | 40462.38 | 63.92 |
| 10.72 | 0.13 | 8.25 | 15279.74 | 24.14 |
| 11.98 | 0.15 | 7.39 | 9563.74 | 15.11 |
| 12.48 | 0.15 | 7.10 | 14996.68 | 23.69 |

TABLE 17-continued

XRPD Data Table

| Pos. [°2θ] | FWHM [°2θ] | d-spacing [Å] | Height [cts] | Rel. Int. [%] |
|---|---|---|---|---|
| 13.25 | 0.18 | 6.68 | 13655.34 | 21.57 |
| 14.38 | 0.15 | 6.16 | 10404.72 | 16.44 |
| 14.69 | 0.15 | 6.03 | 11131.10 | 17.58 |
| 15.11 | 0.20 | 5.87 | 23166.31 | 36.60 |
| 15.90 | 0.13 | 5.58 | 6572.05 | 10.38 |
| 16.30 | 0.20 | 5.44 | 38727.58 | 61.18 |
| 17.13 | 0.23 | 5.18 | 63299.61 | 100.00 |
| 17.74 | 0.17 | 5.00 | 15095.93 | 23.85 |
| 18.23 | 0.20 | 4.87 | 14190.89 | 22.42 |
| 19.78 | 0.20 | 4.49 | 11371.71 | 17.96 |
| 20.29 | 0.18 | 4.38 | 28258.72 | 44.64 |
| 20.88 | 0.20 | 4.25 | 11394.74 | 18.00 |
| 21.69 | 0.10 | 4.10 | 7304.56 | 11.54 |
| 21.92 | 0.18 | 4.06 | 9295.19 | 14.68 |
| 25.01 | 0.17 | 3.56 | 8487.99 | 13.41 |
| 25.44 | 0.15 | 3.50 | 8971.11 | 14.17 |
| 25.62 | 0.23 | 3.48 | 7561.08 | 11.94 |

TABLE 18

Solid State $^{13}$C NMR Data

| Peak | v(F1) [ppm] | Intensity [abs] | Intensity [rel] |
|---|---|---|---|
| 1 | 174.30 | 3342800.86 | 5.47 |
| 2 | 151.76 | 4875738.84 | 7.98 |
| 3 | 143.08 | 4937517.05 | 8.08 |
| 4 | 141.47 | 4895517.41 | 8.01 |
| 5 | 139.72 | 5473393.72 | 8.95 |
| 6 | 134.99 | 5045623.66 | 8.25 |
| 7 | 133.87 | 4070943.45 | 6.66 |
| 8 | 133.18 | 6027611.34 | 9.86 |
| 9 | 130.53 | 5629472.55 | 9.21 |
| 10 | 128.11 | 4354315.61 | 7.13 |
| 11 | 124.60 | 2996501.88 | 4.90 |
| 12 | 123.10 | 3691109.91 | 6.04 |
| 13 | 115.91 | 3157834.66 | 5.17 |
| 14 | 85.23 | 6108149.53 | 10.00 |
| 15 | 78.05 | 2851707.20 | 4.67 |
| 16 | 65.65 | 4420846.34 | 7.23 |
| 17 | 61.80 | 2795012.02 | 4.57 |
| 18 | 60.23 | 6067426.56 | 9.93 |
| 19 | 57.78 | 3987290.50 | 6.52 |
| 20 | 57.28 | 4156007.39 | 6.80 |
| 21 | 56.15 | 3763019.48 | 6.16 |
| 22 | 54.40 | 3012506.42 | 4.93 |
| 23 | 51.84 | 4997182.81 | 8.17 |
| 24 | 50.30 | 3249618.88 | 5.32 |

TABLE 18-continued

| | Solid State ¹³C NMR Data | | |
| --- | --- | --- | --- |
| Peak | v(F1) [ppm] | Intensity [abs] | Intensity [rel] |
| 25 | 49.53 | 4677813.33 | 7.66 |
| 26 | 43.15 | 5294261.23 | 8.67 |
| 27 | 39.48 | 2715242.14 | 4.44 |
| 28 | 38.27 | 3420418.53 | 5.60 |
| 29 | 36.84 | 3868181.97 | 6.33 |
| 30 | 31.05 | 3434460.58 | 5.62 |
| 31 | 30.09 | 3714100.47 | 6.08 |
| 32 | 27.75 | 2815977.80 | 4.61 |
| 33 | 25.54 | 3625318.16 | 5.93 |
| 34 | 24.04 | 2903757.64 | 4.75 |
| 35 | 20.39 | 2695161.47 | 4.41 |
| 36 | 19.13 | 4118642.73 | 6.74 |
| 37 | 13.57 | 3585801.05 | 5.87 |

Single Crystal Data: A dry powder sample of AMG 397 crystalline hydrate form was used for single crystal structure determination. The specimen chosen for data collection was a needle with the approximate dimensions 0.002×0.008× 0.025 mm³. The crystal was mounted on a MiTeGen™ mount with mineral oil (STP Oil Treatment). First diffraction patterns showed the crystal to be of marginal quality giving rise to smeared, elongated and split reflections, and diffracting only weakly.

Diffraction data (φ- and ω-scans) were collected at 100K on a Bruker-AXS X8 Kappa diffractometer coupled to a Bruker APEX2 CCD detector using Cu Kα radiation (λ=1.54178 Å) from an /μS microsource. Data reduction was carried out with the program SAINT[1] and semi-empirical absorption correction based on equivalents was performed with the program SADABS[2]. A summary of crystal properties and data/refinement statistics is given in table 19.

The structure of AMG 397 crystalline hydrate was determined at 100K in the monoclinic chiral space group P21 with one molecule of AMG 397 and 80% of a water molecule in the asymmetric unit.

TABLE 19

| X-ray Single Structure Data | | |
| --- | --- | --- |
| Wavelength | 1.54178 Å | |
| Crystal system | Monoclinic | |
| Space group | P2₁ | |
| Unit cell dimensions | a = 10.9544(10) Å | α = 90° |
| | b = 13.6828(9) Å | β = 92.724(6)° |
| | c = 13.4164(9) Å | γ = 90° |
| Volume | 2008.7(3) Å³ | |
| Z | 2 | |
| Density (calculated) | 1.289 Mg/m³ | |
| Absolute structure parameter | −0.008(18) | |

What is claimed is:

1. A solid dispersion comprising amorphous AMG 397 or a pharmaceutically acceptable salt or solvate thereof, and a polymer, wherein AMG 397 has a structure wherein the amorphous AMG 397 has an endothermic transition at 188° C. to 205° C., as measured by differential scanning calorimetry.

2. The solid dispersion of claim 1, wherein the amorphous AMG 397 is characterized by an XRPD pattern indicative of an amorphous solid, comprising a broad diffuse scattering peak.

3. The solid dispersion of claim 1 wherein the endothermic transition is at 196° C. ±3° C.

4. The solid dispersion of claim 1, wherein the amorphous AMG 397 has a moisture sorption profile that shows a weight gain of about 6.4%.

5. The solid dispersion of claim 1, wherein the polymer comprises pulluan, dextrin, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate dimethylaminoacetate, a copolymer of vinyl diethylamine/ vinyl acetate, a copolymer of vinyl benzylamine/vinyl acetate, polyvinyl acetaldiethylamino acetate, a copolymer of vinylpiperidylacetoacetal/vinyl acetate, polydiethylaminomethylstyrene, a copolymer of methyl methacrylate/butyl methacrylate/dimethylaminoethyl methacrylate and polydimethylaminoethylmethacrylate, a copolymer of 2-methyl-5-vinylpyridine/methylmethacrylate/methacrylic acid, a copolymer of 2-methyl-5- vinylpyridine/methyl acrylate/methacrylic acid, a copolymer of 2-vinyl-5-ethylpyridine/methacrylic acid/methyl acrylate, a copolymer of 2-vinylpyridine/methacrylic acid/acrylonitrile, carboxymethylpiperidyl starch, carboxy-methylbenzylaminocellulose, a copolymer of N-vinylglycine/styrene, chitosan, poly (vinyl alcohol), maleic anhydride copolymer, poly (vinyl pyrolidone), starch, starch-based polymer, poly (2-ethyl-2-oxazoline), poly(ethyleneimine), polyurethane hydrogel, welan gum, rhamsan gum, polyvinyl acetate, ethylcellulose, eudragit RL, eudragit RS, eudragit NE 30D, Kollicoat EMM 30D, or a combination thereof.

6. The solid dispersion of claim 1, wherein the polymer comprises hydroxypropyl methylcellulose, hydroxypropylmethylcellulose acetate succinate, polyvinylpyrrolidone, polyvinyl alcohol, poly (vinyl pyrrolidone), hydroxypropylcellulose, or a combination thereof.

7. The solid dispersion of claim 1, wherein the amorphous AMG 397 is present in an amount of 1% to 90%, based on the total weight of the solid dispersion.

8. The solid dispersion of claim 7, wherein the amorphous AMG 397 is present in an amount of 20% to 60%, based on the total weight of the solid dispersion.

9. The solid dispersion of claim 8, wherein the amorphous AMG 397 is present in an amount of 50% to 60%, based on the total weight of the solid dispersion.

10. The solid dispersion of claim 1, wherein amorphous AMG 397 and the polymer are present at 50 wt % each.

11. The solid dispersion of claim 1, wherein amorphous AMG 397 is present at 25 wt % and the polymer is present at 75 wt %.

12. The solid dispersion of claim 1, wherein amorphous AMG 397 is present at 75 wt % and the polymer is present at 25 wt %.

13. The solid dispersion of claim 1, wherein upon storage at 40° C. and 75% relative humidity in an open container for 1 month, exhibits less than 3% total impurities.

14. The solid dispersion of claim 1, wherein upon storage at 40° C. and 75% relative humidity in a closed container for 1 month, exhibits less than 2% total impurities.

15. The solid dispersion of claim 1, having a D50, as measured by laser diffraction, of less than 3 μm.

16. The solid dispersion of claim 15, having a D90, as measured by laser diffraction, of less than 7 μm.

17. A pharmaceutical formulation comprising the solid dispersion of claim 1 and a pharmaceutically acceptable excipient.

18. The pharmaceutical formulation of claim 17, in the form of a tablet.

19. The pharmaceutical formulation of claim 17, further comprising a surfactant.

20. The pharmaceutical formulation of claim 19, wherein the surfactant comprises a non-ionic surfactant.

21. The pharmaceutical formulation of claim 20, wherein the surfactant comprises a polysorbate, a poloxamer, or a combination thereof.

22. The pharmaceutical formulation of claim 20, wherein the surfactant comprises polysorbate 20, polysorbate 60, polysorbate 80, or a combination thereof.

23. The pharmaceutical formulation of claim 17, wherein amorphous AMG 397 has a bioavailability (% F) of at least 15% within 24 hours, as assessed in a beagle dog PK study over 48 hours.

24. The pharmaceutical formulation of claim 23, wherein the bioavailability of amorphous AMG 397 is at least 15% when a subject's stomach is at a pH of 6-7.

25. The pharmaceutical formulation of claim 23, wherein the bioavailability of amorphous AMG 397 is at least 15% when a subject's stomach is at a pH of 2-3.

26. The pharmaceutical formulation of claim 23, wherein amorphous AMG 397 has a bioavailability (% F) of at least 25% within 48 hours, as assessed in a beagle dog PK study over 48 hours, when co-administered with P-gp inhibitor.

27. A method of treating a subject suffering from cancer, comprising administering to the subject a therapeutically effective amount of the pharmaceutical formulation of claim 19.

28. The method of claim 27, wherein the cancer is multiple myeloma, non-Hodgkin's lymphoma, or acute myeloid leukemia.

29. A method of preparing the solid dispersion of claim 1 comprising admixing amorphous AMG 397 and the polymer in a solvent to form a solution, and spray-drying the solution to form the solid dispersion.

30. The method of claim 29, wherein the solvent comprises an organic solvent or water.

31. The method of claim 30, wherein the solvent comprises an aprotic organic solvent.

32. The method of claim 31, wherein the solvent comprises dichloromethane (DCM), tetrahydrofuran (THF), or a combination thereof.

33. The method of claim 32, wherein solvent comprises water and DCM, THE, or a combination of DCM and THF.

34. The method of claim 29, further comprising drying the solid dispersion.

35. The method of claim 29, further comprising formulating the solid dispersion into a pharmaceutical formulation.

\* \* \* \* \*